(12) United States Patent
Takeuchi et al.

(10) Patent No.: US 7,089,813 B2
(45) Date of Patent: Aug. 15, 2006

(54) MASS SENSOR AND MASS SENSING METHOD

(75) Inventors: Yukihisa Takeuchi, Nishikamo-Gun (JP); Takao Ohnishi, Nishikasugai-Gun (JP); Koji Kimura, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 11/060,988

(22) Filed: Feb. 18, 2005

(65) Prior Publication Data

US 2005/0145032 A1    Jul. 7, 2005

Related U.S. Application Data

(62) Division of application No. 10/925,514, filed on Aug. 25, 2004, which is a division of application No. 10/465,470, filed on Jun. 19, 2003, now Pat. No. 6,840,123, which is a division of application No. 10/071,019, filed on Feb. 8, 2002, now Pat. No. 6,612,190, which is a division of application No. 09/297,655, filed as application No. PCT/JP98/03969 on Sep. 4, 1998, now Pat. No. 6,386,053.

(30) Foreign Application Priority Data

Sep. 8, 1997   (JP)   ................................... 9-243073
Dec. 26, 1997  (JP)   ................................... 9-361368

(51) Int. Cl.
   *G01G 9/00* (2006.01)
(52) U.S. Cl. ...................................................... 73/865
(58) Field of Classification Search ............. 73/514.29, 73/514.34, 24.06, 24.03, 865; 118/712; 435/30
   See application file for complete search history.

(56) References Cited

U.S. PATENT DOCUMENTS

| 3,164,004 A |   | 1/1965  | King, Jr. |
|---|---|---|---|
| 3,581,579 A | * | 6/1971  | Schmidlin et al. ....... 73/514.11 |
| 4,215,570 A |   | 8/1980  | Eer Nisse |
| 4,399,686 A |   | 8/1983  | Kindlund et al. |
| 4,517,841 A |   | 5/1985  | Peters et al. |
| 4,548,079 A |   | 10/1985 | Klatt |
| 4,789,804 A |   | 12/1988 | Karube et al. |
| 5,079,958 A | * | 1/1992  | Takase et al. .......... 73/862.625 |
| 5,121,180 A |   | 6/1992  | Beringhause et al. |
| 5,209,119 A |   | 5/1993  | Polia et al. |
| 5,349,844 A | * | 9/1994  | Lilienfeld ................... 73/28.01 |
| 5,668,303 A |   | 9/1997  | Giesler et al. |
| 5,827,947 A |   | 10/1998 | Miller et al. |
| 5,952,572 A |   | 9/1999  | Yamashita et al. |

(Continued)

FOREIGN PATENT DOCUMENTS

EP            0 152 700           8/1985

(Continued)

*Primary Examiner*—Robert Raevis
(74) *Attorney, Agent, or Firm*—Burr & Brown

(57) ABSTRACT

A mass sensor in which a connection plate and a diaphragm are joined together at their respective sides; a sensing plate is joined to the connection plate at their respective sides in the direction perpendicular to the direction where the diaphragm is joined to the connection plate; a piezoelectric element consisting of a piezoelectric film and an electrode is installed on at least either one of plate surfaces of the sensing plate; and a resonating portion consisting of the diaphragm, the sensing plate, the connection plate, and the piezoelectric element is joined to a sensor substrate. Change in the mass of the diaphragm is measured by measuring change in the resonant frequency of the resonating portion accompanying the change in the mass of the diaphragm.

1 Claim, 19 Drawing Sheets

U.S. PATENT DOCUMENTS 6,457,361 B1 10/2002 Kimura et al.

FOREIGN PATENT DOCUMENTS

| EP | 0 614 087 | 4/1991 |
| GB | 2 236 855 | 4/1991 |
| JP | 61-231419 | 10/1986 |
| JP | 62-064934 | 3/1987 |
| JP | 63-200028 | 8/1988 |

* cited by examiner

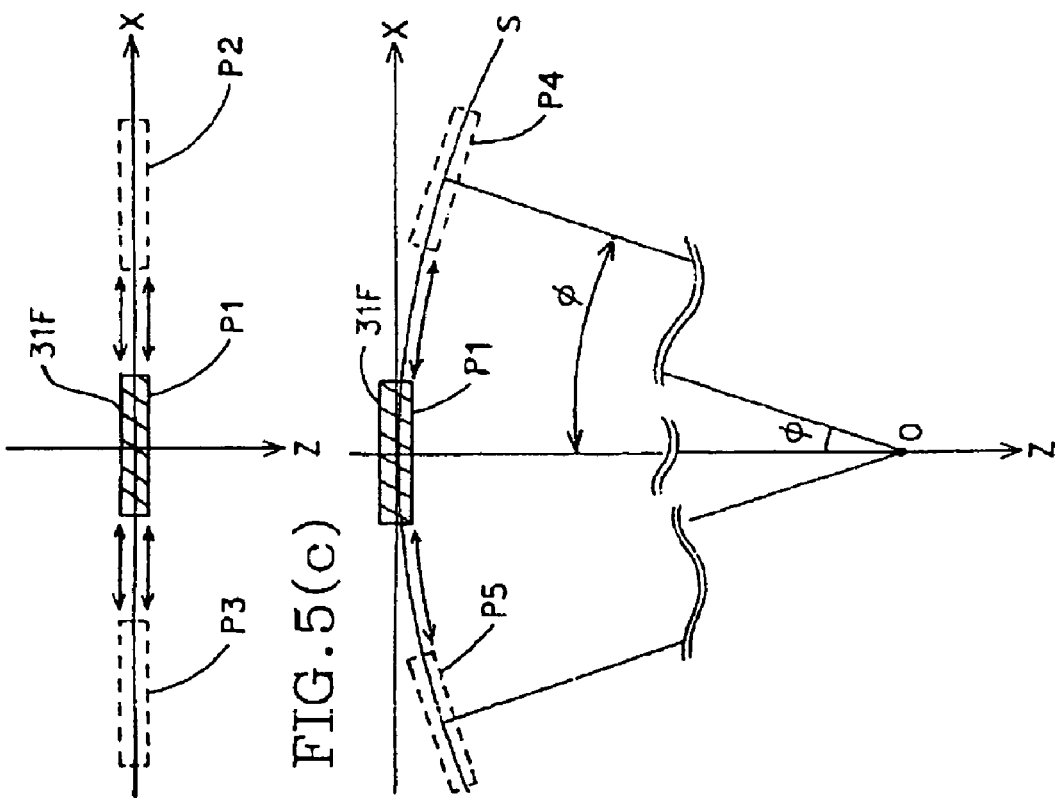
FIG.5(a)
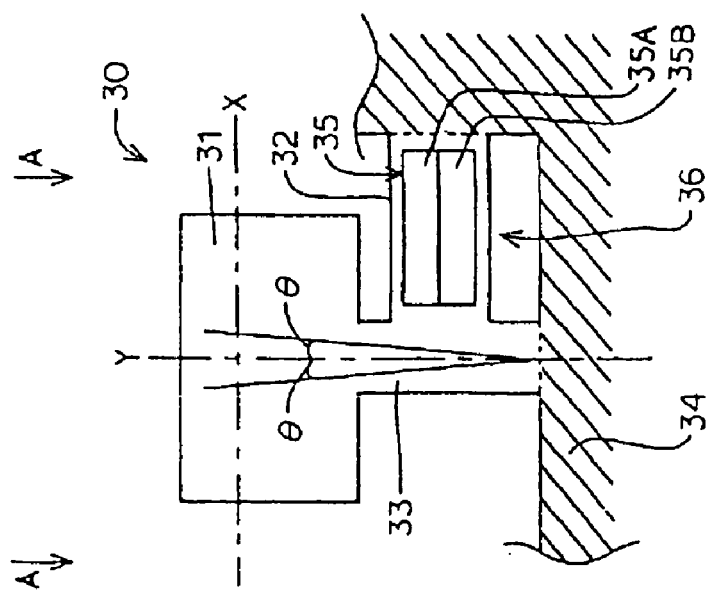
FIG.5(b)
FIG.5(c)

FIG.7(a)
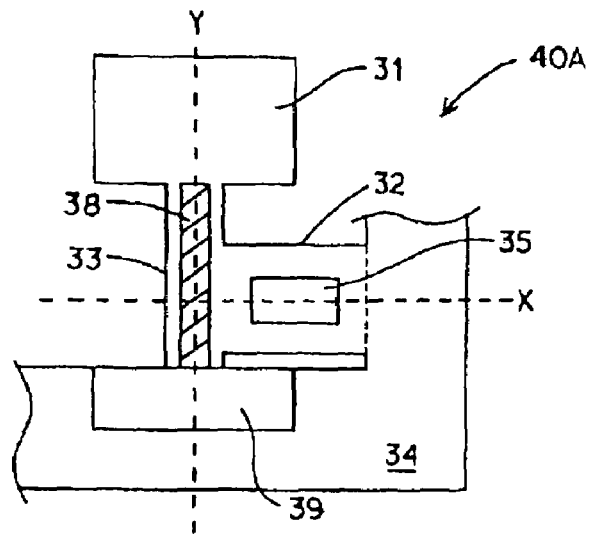
FIG.7(b)
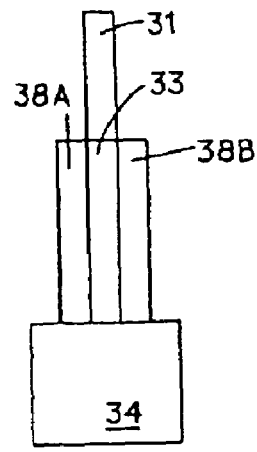
FIG.7(c)  FIG.7(d)  FIG.7(e)
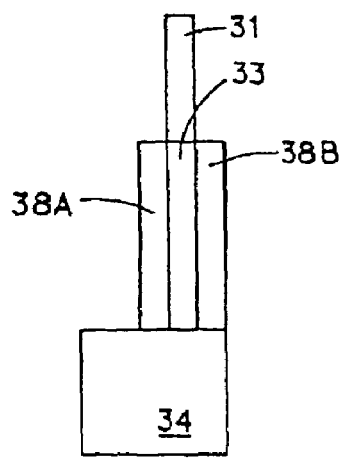 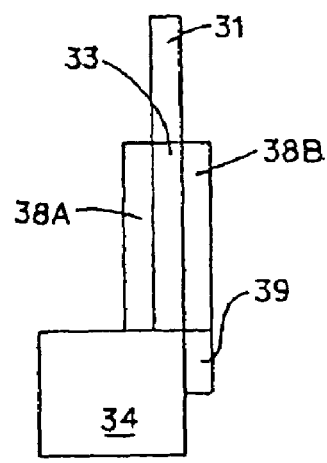 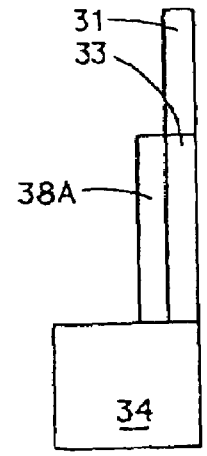

MASS SENSOR AND MASS SENSING METHOD

CROSS REFERENCE TO RELATED APPLICATIONS

This application is a division of U.S. application Ser. No. 10/925,514, filed Aug. 25, 2004, now allowed, which in turn is a division of U.S. application Ser. No. 10/465,470, filed Jun. 19, 2003, now U.S. Pat. No. 6,840,123, which is a division of U.S. application Ser. No. 10/071,019, filed Feb. 8, 2002, now U.S. Pat. No. 6,612,190, which is a division of U.S. application Ser. No. 09/297,655, filed May 4, 1999, now U.S. Pat. No. 6,386,053, which was the National Stage of International Application No. PCT/JP98/03969, filed Sep. 4, 1998, the entireties of which are incorporated herein by reference.

FIELD OF THE INVENTION

The present invention relates to a mass sensor for determining a minute mass of a nanogram ($10^{-9}$ g) order, for example, a mass sensor for sensing microorganisms such as bacteria, viruses, and protozoa (immune sensor), and a mass sensor for sensing moisture, toxic substances, or specific chemical substances such as taste components (moisture meter, gas sensor, and taste sensor), and a method for sensing a mass. In particular, the present invention relates to a mass sensor, and a method for sensing a mass, conveniently used for determining the mass of a body to be sensed by measuring change in resonant frequencies caused by changes in the mass of the diaphragm on which a catching substance for catching a body to be sensed by reacting only with the body to be sensed is applied.

Since the mass sensor of the present invention is not limited to the measurement of change in the mass of the catching substance applied on a diaphragm as described above, that is, not limited to the indirect measurement of change in the mass of a diaphragm, but it is naturally possible to sense change in resonant frequency due to change in the mass of the diaphragm itself, the mass sensor can also be used as a thickness meter for vapor-deposited films or a dew point meter.

Furthermore, even if the mass of the diaphragm is not changed directly or indirectly, the mass sensor of the present invention can also be used as a vacuum meter, a viscosity meter, or a temperature sensor by placing it in an environment to cause change in resonant frequency, that is, by placing it in an environment of medium gases or liquids having different degrees of vacuum, viscosity, or temperature.

Thus, although the mass sensor of the present invention can be used in various applications depending on its embodiments, the same basic principle is also applied to the measurement of change in resonant frequencies of the diaphragm and the resonating portion including the diaphragm.

BACKGROUND OF THE INVENTION

Recent progress of scientific and medical technologies, and newly developed medicines such as antibiotics and chemicals have enabled the treatment of various diseases heretofore considered to be difficult to treat. On the other hand, especially in developed countries where people are accustomed in such medical civilization, immunological resistance of human beings have lowered, and many people have suffered from various diseases caused by substances or microorganisms which heretofore had not hurt human beings.

Among what are referred to as diseases, microorganism examinations are essential for the treatment of diseases caused by microorganisms such as bacteria, viruses, or protozoa, to find their pathogens, to clarify their types, and to determine drugs to which they are sensitive.

At present, in the first stage of microorganism examinations, since the cause of a disease and the type of the pathogen can be estimated from the symptoms, various specimens, such as blood, are selected depending on the type of the disease, pathogens present in the specimens are morphologically identified, or antigens or the specific metabolites of pathogens (e.g., toxins or enzymes, etc.) existing in the specimens are immunochemically identified. This process is smear, tinction, or microscopy used in bacterial examinations, and in recent years, instantaneous identification has become possible in this stage by fluorescent antibody tinction or enzymatic antibody tinction.

Furthermore, the virus serological test, recently used in the detection of viruses, is a method for proving the presence of specific immunity antibodies that appear in the serum of a patient. Examples of the method include the complement fixation reaction in which the presence of antibodies or antigens is determined by adding complements to test blood, and by observing whether the complements react with antigens or antibodies in the blood and fix to the cell membranes of the antigens or antibodies, or destroy the cell membranes.

Except extremely special cases where symptoms have not been seen heretofore, and the disease is caused by a new pathogen which has not been discovered, in the treatment of diseases caused by microorganisms or the like, adequate treatment can be conducted by finding pathogens in an early stage through the microorganism test described above, and the patient can be led to recovery without worsening of the symptoms.

However, with methods such as smear, tinction, and microscopy, the detection of microorganisms is often difficult depending on their quantities, and time-consuming treatment such as the culture of specimens on an agar is required at need. Also in the virus serological test, since measurements must be performed as a rule during both the acute stage and the convalescent stage for determination from the movement of the quantities of antibodies, there is the problem of time consumption from the point of view of prompt diagnosis.

As seen in complement fixation described above, when a substance to be sensed reacts with a catching substance which catches the substance to be sensed by reacting only with specific substance to be sensed, microorganisms, the mass of the catching substance increases by the mass of the substance to be sensed, even slightly. Such an increase in the mass similarly occurs in the relationship between a catching substance and a chemical substance such as a specific gaseous substance and a smell component, and also applies to the case where a substrate itself without change in the mass is a catching substance, on which a specific substance is deposited or added. On the contrary, when a reaction in which a substance to be sensed caught by a catching substance or the like is released occurs, the mass of the catching substance or the like slightly decreases.

As an example of a method for sensing change in such a small mass, U.S. Pat. No. 4,789,804 discloses in FIG. 27 thereof a mass sensor 80 comprising a quartz oscillator 81 and electrodes 82, 83 facing the quartz oscillator. When any substance adheres externally on these electrodes 82, 83, the mass sensor 80 senses change in their mass using change in the resonant frequency of the thickness slip oscillation of the quartz oscillator 81 in the direction of the surface of the electrodes. Since such a mass sensor 80 measures change in resonant frequency basically caused by change in the mass load on the quartz oscillator 81, such a mass sensor 80 is considered to be able to be used also as a thickness meter for measuring the thickness or the growth of a vapor-deposited film, or a moisture meter.

However, when such a quartz oscillator 81 is used, since the part on which an external substance adheres and the part for detecting resonant frequency are in the same location, for example, the resonant frequency is unstable when the piezoelectric properties of the mass sensor 80 itself vary due to the temperature of the specimen or change in temperature. Also, if the specimen is a conductive solution, and when the mass sensor 80 is immersed unprotected in the specimen, a short-circuit between electrodes may occur. Therefore, the mass sensor 80 must be subjected to insulation such as resin coating.

SUMMARY OF THE INVENTION

The present invention aims to solve the above problems of a micro-mass sensor, and according to the present invention, there are provided first to sixth mass sensors described below.

As a first mass sensor, there is provided a mass sensor characterized in that a piezoelectric element is arranged on at least a part of at least one plate surface of a sensing plate, a side of at least one sheet-like diaphragm is joined to a side of said sensing plate so that the plate surface of said diaphragm is perpendicular to the plate surface of said sensing plate, the other side of said sensing plate is joined to a sensor substrate, and a resonance portion is formed of said sensing plate, said diaphragm, and said piezoelectric element.

Furthermore, as a second mass sensor, there is provided a mass sensor characterized in that a connection plate is joined to a diaphragm at respective sides, a sensing plate is joined to said connection plate at respective sides in the direction perpendicular to the joining direction of said diaphragm and said connection plate, a piezoelectric element is arranged on at least a part of at least one of the plate surfaces of said sensing plate, at least a part of sides of said connection plate and said sensing plate is joined to a side of the sensor substrate, and a resonance portion is formed of said diaphragm, said connection plate, said sensing plate, and said piezoelectric element.

Furthermore, as a third mass sensor, there is provided a mass sensor characterized in that a connection plate is joined to a diaphragm at respective sides, two sensing plates are joined to said connection plate at respective sides in the direction perpendicular to the joining direction of said diaphragm and said connection plate so as to sandwich said connection plate, a piezoelectric element is arranged on at least a part of at least one of the plate surfaces of at least one of said sensing plates, at least a part of sides of said connection plate and said sensing plates is joined to a side of the sensor substrate, and a resonance portion is formed of said diaphragm, said connection plate, said sensing plates, and said piezoelectric element.

Here, in the third mass sensor, it is preferable that said piezoelectric element is arranged on at least one of the plate surfaces of one of said respective sensing plates facing to each other via the connection plates, and one or more, preferably a plurality of, slits are formed on the other sensing plate in the direction perpendicular to the joining direction of said other sensing plate and said connection plate. It is also preferable that respective piezoelectric elements are arranged on the plate surfaces of said respective sensing plates facing to each other via the connection plates in at least the same direction, and that the polarizing direction of the piezoelectric film in said piezoelectric elements arranged on one of the sensing plates, and the polarizing direction of the piezoelectric film in said piezoelectric elements arranged on the other sensing plate are opposite to each other with respect to the connection plates.

Next as a fourth mass sensor, there is provided a mass sensor characterized in that a connection plate and a sensing plate not directly joined to each other are joined to said diaphragm at respective sides so that the joining directions with the diaphragm are parallel to each other, said connection plate and said sensing plate are joined to one side of a sensor substrate, a piezoelectric element is arranged on at least a part of at least one of the plate surfaces of said sensing plate, and a resonance portion is formed of said diaphragm, said connection plate, said sensing plate, and said piezoelectric element.

As a fifth mass sensor, there is provided a mass sensor characterized in that an assembly of a diaphragm sandwiched with two connection plates by joining at respective sides is placed across the side surfaces of a depression formed on a sensor substrate, each of two sensing plates is placed across said connection plate and across the bottom side of said depression in the direction perpendicular to the direction of said respective connection plates sandwiching said diaphragm, a piezoelectric element is arranged on at least a part of at least one of the plate surfaces of said sensing plates, and a resonance portion is formed of said diaphragm, said connection plate, said sensing plates, and said piezoelectric element.

Here, a depression means that formed from sides facing to each other and the bottom side connecting such sides; however, in the present invention, the bottom side is not necessarily a plane, but the shape of the bottom side may be changed variously unless the measurement of the oscillation and the resonant frequency of the diaphragm, such as the provision of a depression or a projection in the bottom side, is affected.

As a sixth mass sensor, there is provided a mass sensor characterized in that an assembly of a diaphragm sandwiched with two connection plates by joining at respective sides is placed across a through-hole formed on a sensor substrate, at least a plurality of sensing plates are placed between said respective connection plates and the side of said through-hole, or said diaphragm and the side of said through-hole, in the direction perpendicular to the direction of said respective connection plates sandwiching said diaphragm, a piezoelectric element is arranged on at least a part of at least one of the plate surfaces of at least one of said sensing plates, and a resonance portion is formed of said diaphragm, said connection plates, said sensing plates, and said piezoelectric element.

Here, in the sixth mass sensor, when the piezoelectric element is arranged on at least one of the plate surfaces in each pair of said respective sensing plates facing to each other via the connection plates or the diaphragm, it is preferable that one or more, preferably a plurality of, slits are formed on the other sensing plate in the direction perpendicular to the joining direction of said other sensing plate and said respective connection plates. Also, when respective piezoelectric elements are arranged on the plate surface of each pair of said respective sensing plates facing to each other via the connection plates or the diaphragm in at least the same direction, it is preferable that the polarizing direction of the piezoelectric film in said piezoelectric elements arranged on one of the sensing plates, and the polarizing direction of the piezoelectric film in said piezoelectric elements arranged on the other sensing plate is opposite to each other with respect to the connection plates or the diaphragm.

In these second through sixth mass sensors, it is preferable that the diaphragm, the connection plate, and the sensing plate form a same plane when joined to each other, that is, these members have almost the same thickness. It is also preferable that the sensing plate is fitted in and joined to the depression formed by the connection plate and the sensor substrate. It is preferable for this that the diaphragm, the connection plate, and the sensing plate are integrally formed from a diaphragm, and the sensor substrate is laminated integrally with the diaphragm and the base plate.

It is also preferable that a spring plate is bonded to one of or each of plate surfaces of the connection plate, and this spring plate is joined to the sensor substrate or the spring plate reinforcement. At this time, unlike the structure bonded using adhesives, it is preferable that the spring plate is integrally formed with an intermediate plate integrally inserted between the diaphragm and the base plate, or integrally formed with the spring plate reinforcement integrally formed with the diaphragm, and also integrally formed with the connection plate. When a plurality of connection plates are used, it is preferable that the assemblies of the connection plate and the spring plate have the same shape. It is also preferable that the mass sensor has a reinforcing plate joined to the side of said sensor substrate, and in this case, it is preferable that the reinforcing plate is integrally formed with the spring plate and the sensor substrate.

Since a catching substance reacting only with a substance to be sensed and catching the substance to be sensed is applied on the diaphragm, the piezoelectric element measures change in the resonant frequency of the resonating portion in the state when the substance to be sensed has not been caught by the catching substance, and in the state after the substance to be sensed has been caught by said catching substance, all the mass sensors according to the present invention are suitably used in applications to measure the mass of the substance to be sensed caught by the catching substance.

It is preferable that at least two resonating portions are placed on the sensor substrate, and the catching substance is not applied to one of the diaphragm of the resonating portions to use this diaphragm for referencing. On the other hand, it is also preferable that different catching substances are applied to each resonating portion, that is, a plurality of resonating portions to which more than one of different catching substances are separately applied are provided in a sensor. Here, more than one resonating portion may be placed on the sensor substrate so as to expand the dynamic range by integrating the signals from the respective resonating portions. Also, a through-hole of an optional shape may be formed inside said sensor substrate, and the resonating portion may be formed on the internal circumferential surface of the through-hole.

It is also preferable, to improve sensitivity, that one of the piezoelectric element is split into two portions; one is used for driving and the other is used for sensing. Furthermore, it is preferable, to improve sensitivity, that two piezoelectric elements are placed on one resonating portion, and one of the piezoelectric elements is used for driving and the other is used for sensing. Therefore, each of the two piezoelectric elements placed on a resonating portion may be further split into two portions, and in this case, each of the two piezoelectric elements has both driving and sensing functions.

Furthermore, when the specimen is a conductive solution, it is preferable to provide a position sensor consisting of a pair of electrodes on the middle between the diaphragm and the piezoelectric element on the sensor substrate, so that the diaphragm is immersed in the solution but the piezoelectric element is not immersed in the solution even if the mass sensor is immersed, so as to install the mass sensor on a suitable position. Even if the specimen is a conductive solution, the electrodes or other parts can be prevented from short-circuiting, if the piezoelectric element, the electrodes of the piezoelectric element and electrode leads connected to the electrode, are coated with a resin or glass insulation coating layer. Furthermore, it is preferable that a shield layer consisting of a conductive material is formed on the surface of said insulation coating layer, so as to reduce noise such as external electromagnetic waves.

It is preferable that the sensor substrate, diaphragm, connection plate, sensing plate, and spring plate constituting a mass sensor of the present invention are integrally composed of stabilized zirconia or partially stabilized zirconia. As the material for the piezoelectric film in the piezoelectric element, a material containing a component mainly consisting of lead zirconate, lead titanate, and lead magnesium niobate is suitably used, oscillation modes, adjusting the resonant frequencies and sensitivity can be controlled if the shapes of the diaphragm, connection plate, sensing plate, or spring plate are dimensionally adjusted by trimming with laser processing or machining. It is further preferable that the electrode of the piezoelectric element is laser-processed or machined to adjust the effective electrode area of the piezoelectric element.

The term "piezoelectric" used herein includes piezoelectricity and electric distortion, and what are referred to as a piezoelectric element include electric distortion elements, and piezoelectric ceramics include electric distortion ceramics.

Next, according to the present invention, methods for mass sensing corresponding to the structure of various mass sensors as described above are provided. First, there is provided a method for sensing the mass with the mass sensor in which a side of at least one sheet-like diaphragm is joined to a side of said sensing plate so that the plate surface of said diaphragm is perpendicular to the plate surface of said sensing plate on which a piezoelectric element is installed, and the other side of said sensing plate is joined to the sensor substrate, characterized in measuring with said piezoelectric element resonant frequency on the basis of at least either one of, θ-mode swing oscillation of said diaphragm in which said diaphragm makes pendulum-like oscillation centered on the perpendicular axis perpendicularly passing through the center of a fixed plane, which is the joining surface of said diaphragm and said sensing plate, in the direction perpendicular to the side of said diaphragm and also perpendicular to said perpendicular axis, the φ-mode swing oscillation of said diaphragm in which said diaphragm makes pendulum-like oscillation centered on said perpendicular axis with the swing in the direction perpendicular to the side of said diaphragm and also perpendicular to said perpendicular axis accompanied by the swing in the direction parallel to the side of said diaphragm, or the oscillation of said diaphragm in the direction of said perpendicular axis.

Such a method for mass sensing with a mass sensor is suitably adopted as a method for mass sensing using the first mass sensor according to the present invention as described above from its structure.

Also, according to the present invention there is provided a method for sensing the mass with the mass sensor having at least one piezoelectric element, in which a connection plate is joined to a diaphragm at respective sides, at least one sensing plate is joined to said connection plate at respective sides in the direction perpendicular to the joining direction of said diaphragm and said connection plate, and at least a part of sides of said connection plate and said sensing plate is joined to a part of sides of the sensor substrate, characterized in measuring with said piezoelectric element resonant frequency on the basis of at least either one of, the θ-mode swing oscillation of said diaphragm in which said diaphragm makes pendulum-like oscillation centered on the perpendicular axis perpendicularly passing through the center of a fixed plane, which is the joining surface of said connection plate and said sensor substrate, in the direction perpendicular to the side of said diaphragm and also perpendicular to said perpendicular axis, or the φ-mode swing oscillation of said diaphragm in which said diaphragm makes pendulum-like oscillation centered on said perpendicular axis with the swing in the direction perpendicular to the side of said diaphragm and also perpendicular to said perpendicular axis accompanied by the swing in the direction parallel to the side of said diaphragm.

Such a method for mass sensing with a mass sensor is suitably adopted as a method for mass sensing using the second and third mass sensors according to the present invention as described above from their structures.

Furthermore, according to the present invention there is provided a method for sensing the mass with the mass sensor having at least one piezoelectric element, in which an assembly of a diaphragm sandwiched with two connection plates by joining at respective sides is placed across the side surfaces of a depression or across a through-hole formed on a sensor substrate, at least a plurality of sensing plates are placed between said respective connection plates and the bottom side of said depression or the side of said through-hole, or between said diaphragm and the bottom side of said depression or the side of said through-hole, in the direction perpendicular to the direction of said respective connection plates sandwiching said diaphragm, characterized in measuring with said piezoelectric element resonant frequency on the basis of at least either one of, the θ-mode swing oscillation of said diaphragm in which said diaphragm makes pendulum-like oscillation centered on the perpendicular axis perpendicularly passing through the center of a fixed plane, which is the joining surface of said connection plate and said sensor substrate, in the direction perpendicular to the side of said diaphragm and also perpendicular to said perpendicular axis, the φ-mode swing oscillation of said diaphragm in which said diaphragm makes pendulum-like oscillation centered on said perpendicular axis with the swing in the direction perpendicular to the side of said diaphragm and also perpendicular to said perpendicular axis accompanied by the swing in the direction parallel to the side of said diaphragm, the swing oscillation of said diaphragm centered on said perpendicular axis, oscillating in parallel to the direction perpendicular to the side of said diaphragm and also perpendicular to said perpendicular axis, or the rotating oscillation of said diaphragm in the plate surface of said diaphragm.

Such a method for mass sensing with a mass sensor is suitably adopted as a method for mass sensing using the fifth and sixth mass sensors according to the present invention as described above from their structures, and also suitably adopted as a method for mass sensing using the fourth mass sensor having a structure in which the sensing plate also functions as the connection plate.

According to a mass sensor of the present invention, as described above, change in a minute mass occurring in a diaphragm can be known accurately in a short time from a specific value of change in the resonant frequencies of the resonating portion provided in the mass sensor, and the mass sensor has an advantage of easy measuring operation. Therefore, by placing the mass sensor in an environment changing the resonant frequencies of the resonating portion, various physical and chemical quantities can be measured. For example, the mass sensor of the present invention can be used suitably as a thickness meter for vapor-deposited films and a dew point meter; which utilize direct change in the mass of the diaphragm, a vacuum meter, viscosity meter, and temperature sensor, which utilize the environment where the diaphragm is placed, such as vacuum, viscosity, and temperature; and especially, for the identification of a substance to be sensed and the measurement of its mass by applying to the diaphragm a catching substance which selectively reacts with the substance to be sensed such as a microorganism or a chemical substance in a specimen, and by utilizing change in the mass of such a catching substance.

BRIEF DESCRIPTION OF THE DRAWINGS

For a fully understanding of the nature and objects of the invention, reference should be made to the following detailed description of a preferred mode of practicing the invention, read in connection with the accompanying drawings in which:

FIGS. 5(a)–(c) are diagrams showing another embodiment of a mass sensor of the present invention; (a) is a plan; (b) is a diagram illustrating a θ-mode swing oscillation; and (c) is a diagram illustrating a φ-mode swing oscillation;

FIGS. 7(a)–(e) are diagrams showing still another embodiment of a mass sensor of the present invention; (a) is a plan; and (b) through (e) are sectional views;

DETAILED DESCRIPTION OF THE INVENTION

Figure 1A:
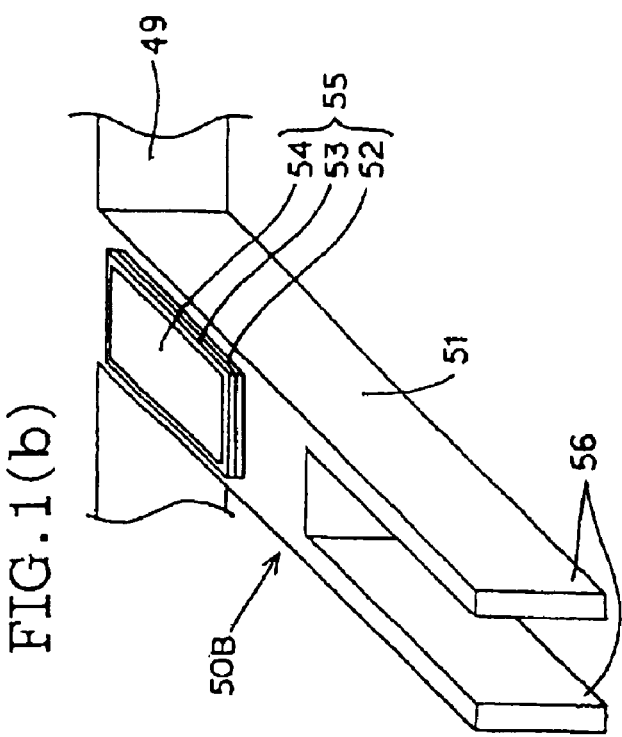
FIGS. 1(a)–(d) are perspective views showing an embodiment of a mass sensor of the present invention; and (a) through (d) are perspective views of the embodiments in which the location and the number of diaphragms are changed.

The embodiments of the present invention will be described below referring to the drawings, in particular focusing on a mass sensor used by applying a catching substance that reacts only with a specific substance to be sensed and catches the specific substance to be sensed to the diaphragm.

However, since the present invention is used in many other applications as described above, the present invention is not in any way limited to the embodiments described below.

FIG. 1(a) is a perspective view showing an embodiment of a mass sensor 50A of the present invention. On the plate surface of at least one sensing plate 51 is provided a piezoelectric element 55 consisting of a first electrode 52, a piezoelectric film 53, and a second electrode 54. The piezoelectric element 55 may be provided on both the surfaces of the sensing plate 51, and the first and second electrodes 52, 54 are connected to an electrode lead (not shown) used for connecting them to a frequency meter or the like.

A sheet-like diaphragm 56 is joined to a side of the sensing plate 51 so that the plate surface of the diaphragm 56 and the plate surface of the sensing plate 51 are perpendicular to each other. Here, "the sides of the sensing plate 51" means a plane perpendicular to the plate surface of the sensing plate 51 on which the piezoelectric element 55 is installed, that is, a plane in the thickness direction, and "a side" means one of the sides. Furthermore, the other side of the sensing plate 51, here, the side opposite to the side to which the diaphragm 56 is joined, is joined to a sensor substrate 49, and a resonating portion is formed of the diaphragm 56, the sensing plate 51, and the piezoelectric element 55, to form the mass sensor 50A.

Here, a diaphragm mainly means the place to cause or to be subject to change in mass, and is an element that oscillates in various modes as described later; a connection plate means an element to connect the diaphragm, sensor substrate, and sensing plate; and a sensing plate means an element that is deformed by the movement of the diaphragm, and transmits the strain to the sensing element, such as a piezoelectric element, installed on the surface, or on the contrary, transmits strain or oscillation generated by a driving element, such as a piezoelectric element, to the diaphragm. The sensor substrate means an element to support the resonating portion, carry various electrode terminals for connecting to measuring instruments, and is used for handling in actual uses.

Methods for using such a mass sensor 50A include, for example, a method in which a catching substance that reacts with and catch only a substance to be sensed is applied to the diaphragm 56, the diaphragm 56 is immersed in a liquid specimen or exposed to a gaseous environment such as a specific gas, to measure change in the resonant frequencies of the mass sensor 50A with the piezoelectric element 55, or a method in which the resonant frequency is measured after the diaphragm 56 is immersed in a liquid specimen and dried in a gas. An example of such a substance to be sensed is an antigen which causes a disease, and an example of the catching substance is an antibody for such an antigen.

Here, the resonant frequency of the mass sensor 50A varies depending on the mass of the resonating portion, in particular, the mass of the diaphragm 56. That is, the resonant frequency of the resonating portion in the state where the substance to be sensed has not been caught by the diaphragm 56 is different from the resonant frequency of the resonating portion in the state where the substance to be sensed has been caught, depending on the mass of the substance to be sensed that has been caught. Therefore, by measuring change in the resonant frequencies using the piezoelectric element 55, the mass of the substance to be sensed caught by the catching substance applied on the diaphragm 56 can be measured.

In the same principle, the mass sensor 50A can be used for measuring decrease in the mass, when the mass of the diaphragm 56 decreases from the mass in the initial state. For example, the mass sensor 50A can be used suitably when the catching substance applied is peeled off for some reason, when the extremely slight corrosion or an extremely small amount of dissolution in a specific solution of the material itself of the diaphragm 56 is to be checked, or for the purpose to measure change in the mass of a specific chemical substance, other than the catching substance, applied to the diaphragm 56 due to the evaporation or dissolution of such a chemical substance.

The structure of such a mass sensor 50A can be summarized to be a structure in which a side of at least one sheet-like diaphragm 56 is joined to a side of a sensing plate 51 so that the plate surface of the diaphragm 56 is perpendicular to the plate surface on which the piezoelectric element 55 of the sensing plate 51 is installed, and the other side of the sensing plate 51 is joined to the sensor substrate 49. Here, as the oscillation mode of the diaphragm used for measuring resonant frequency in the mass sensor 50A, it is preferable to measure the resonant frequency of the resonating portion on the basis of at least either one of oscillation among θ-mode swing oscillation (hereafter referred to as "θ-mode") in which the diaphragm 56 performs pendulum-like oscillation centered on the perpendicular axis (Y-axis) perpendicularly passing through the center of the fixed plane, which is the plane where the diaphragm 56 is joined to the sensing plate 51 in FIG. 1(a), in the direction perpendicular to the side of the diaphragm 56, and also in the direction perpendicular to the Y-axis, that is in the direction of X-axis; φ-mode swing oscillation (hereafter referred to as "φ-mode") in which the diaphragm 56 performs pendulum-like oscillation centered on the Y-axis in the direction perpendicular to the side of the diaphragm 56, and also in the direction perpendicular to the Y-axis, that is in the direction of X-axis, and accompanying swing enlarged in the direction parallel to the side of the diaphragm 56 (Z-axis) as the diaphragm 56 travels apart from the Y-axis; and oscillation in the direction of the Y-axis.

These oscillation modes mean that the direction of the oscillation of the diaphragm 56 is dominant in the directions described above, but the directional components other than the above directions are not completely excluded. This applies also to the citation of oscillation modes on describing various embodiments below.

Since these θ-mode and φ-mode are the same as those in the mass sensor 30 described later, these will be described in detail in the description of the mass sensor 30; however, since these oscillation modes are the rigid body modes utilizing the side of the diaphragm 56, they are suitably used particularly when the diaphragm 56 or the entire mass sensor 50A is immersed in a liquid.

When the mass sensor 50A is used in a gas, the bending mode in which bending in the direction of Z-axis in FIG. 1(a) is dominant can be also effectively used in addition to the above oscillation modes. When the bending mode is used in a liquid, although the effect of the viscosity or density of the liquid is larger than in the above θ-mode and φ-mode, change in mass can be known by measuring resonant frequency. Thus, by detecting voltage induced on the piezoelectric film 53 caused by the oscillation of the diaphragm 56 described above, change in the resonant frequency, or change in the mass of the diaphragm 56 can be known.

Figure 1B:
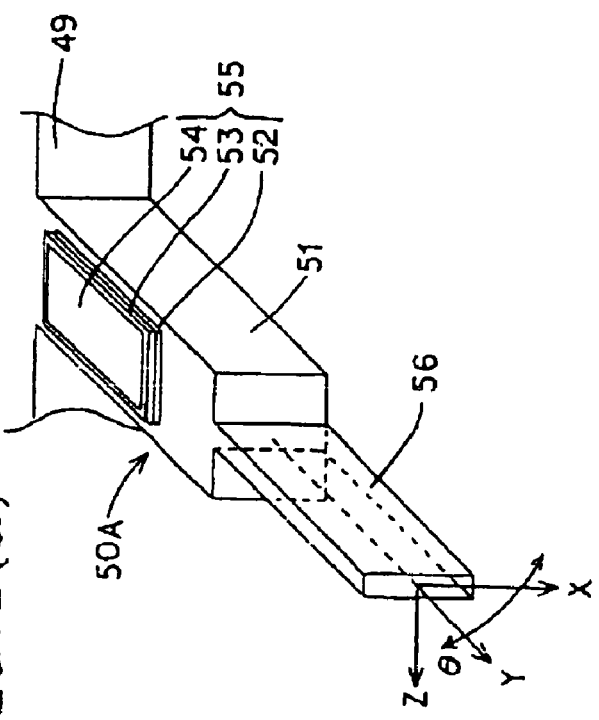
Figure 1C:
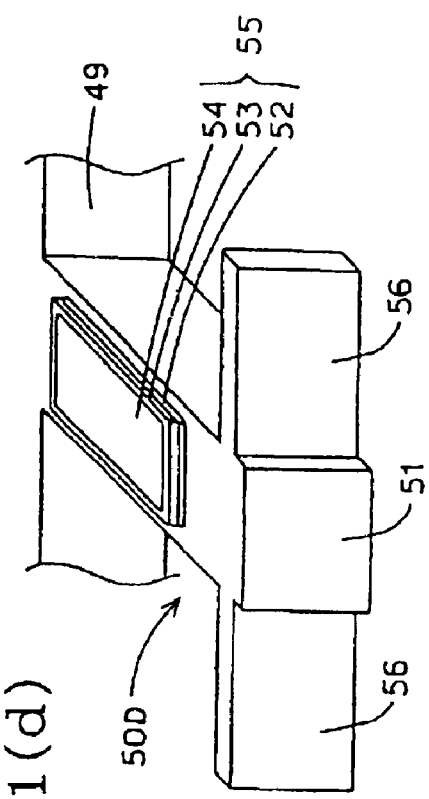
Figure 1D:
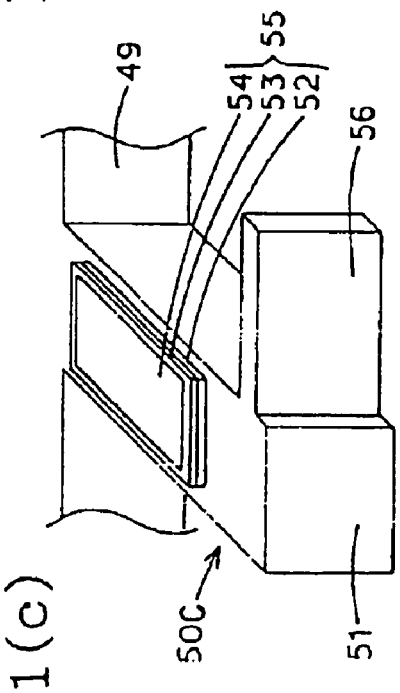

Using the operation principle of the mass sensor 50A described above, those shown in FIGS. 1(b) through 1(d) can be exemplified as embodiments on mass sensors having similar function to the embodiment shown in FIG. 1(a). The mass sensor 50B shown in FIG. 1(b) has two parallel diaphragms 56 similar to the diaphragm 56 in the embodiment of FIG. 1(a) on a side of the sensing plate 51. The use of a plurality of diaphragms 56 can improve the dynamic range of the mass sensor.

The location where a plurality of diaphragms 56 are joined to the sensing plate 51 is not limited as far as it is a side other than the side where the sensing plate 51 is joined to the sensor substrate 49. Also, since at least one diaphragm 56 is required, the diaphragm 56 may be joined to the side perpendicular to the side where the sensing plate 51 is joined to the sensor substrate 49 among the sides of the sensing plate 51 as in the mass sensor 50C shown in FIG. 1(c). Furthermore, each of two diaphragms 56 may be joined to a pair of sides opposite to each other as in the mass sensor 50D shown in FIG. 1(d) to improve dynamic range as in the mass sensor 50B.

At this time, it is preferable that the location where the diaphragm 56 is joined to the sensing plate 51 is in the vicinity of the end of the sensing plate 51 apart from the sensor substrate 49 as much as possible, because the Q-value (peak value, hereafter referred to as "Q-value") of the θ-mode and φ-mode can be increased, that is, the amplitude of the diaphragm 56 is increased, and the sensitivity is improved. Of course, the optional combination of these embodiments of mass sensors 50A–50D shown in FIGS. 1(a) through 1(d) may also be used.

Figure 2:
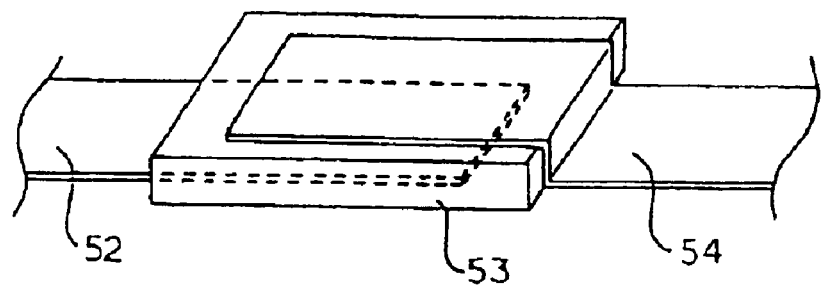
FIG. 2 is a perspective view showing an embodiment of a piezoelectric element installed in a mass sensor of the present invention.
Figure 3:
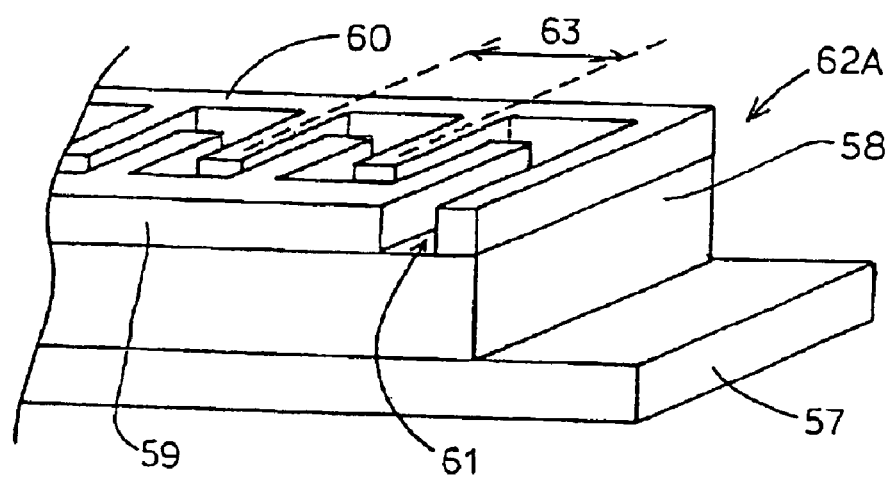
FIG. 3 is a perspective view showing an embodiment of another piezoelectric element installed in a mass sensor of the present invention.

Although the piezoelectric element 55 installed on mass sensors 50A–50D described above is typically of a lamination type in which a first electrode 52, a piezoelectric film 53, and a second electrode 54 are laminated as shown in FIG. 2, a piezoelectric element 62A having a comb structure in which a piezoelectric film 58 is placed on a sensing plate 57 shown in FIG. 3, and a first electrode 59 and a second electrode 60 form gaps 61 of a constant width on the top of the piezoelectric film 58 can also be used. The first electrode 59 and the second electrode 60 in FIG. 3 may be formed in the surface between the sensing plate 57 and the piezoelectric film 58. Furthermore, as shown in FIG. 4, a piezoelectric element 62B in which a piezoelectric film 58 is buried between the comb-shaped first and second electrodes 59, 60 is also suitably used.

Figure 4:
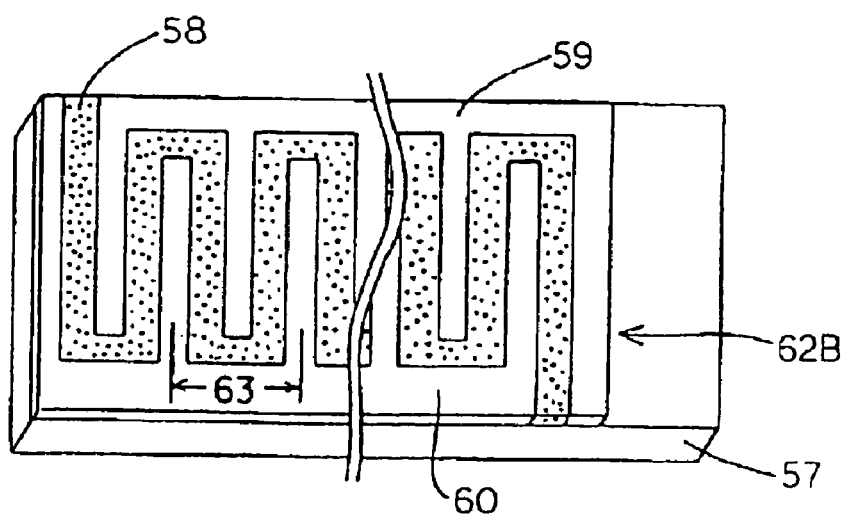
FIG. 4 is a perspective view showing an embodiment of still another piezoelectric element installed in a mass sensor of the present invention.

Here, when a comb-shaped electrode as shown in FIG. 3 or 4 is used, the measuring sensitivity can be raised by reducing the pitch 63. Such piezoelectric elements shown in FIGS. 2 through 4 are used in all the mass sensors of the present invention described later.

Although the measurement of mass as described above can be performed using mass sensors 50A through 50D, increase in detecting sensitivity is limited, because the area of the diaphragm 56 is inevitably small making the area to which a catching substance is applied small, and making change in mass small when the thickness of the vapor-deposited film is measured. Furthermore, warp or bend may occur on the diaphragm 56, and in addition, the mode in which only the diaphragm 56 oscillates may strongly appear. Therefore, it is preferable to modify the structure to that shown in FIG. 5(a) to solve such problems.

That is, FIG. 5(a) is a plan showing another embodiment of a mass sensor of the present invention. In the mass sensor 30, a diaphragm 31 and a connection plate 33 are joined at their respective sides, and a sensing plate 32 is joined to the connection plate 33 at their respective sides in the direction perpendicular to the Y-axis direction, which is the direction where the diaphragm 31 and the connection plate 33 are joined, that is the X-axis direction. A piezoelectric element 35 is installed on at least a part of at least one of the plate surfaces of the sensing plate 32 to constitute a sensing portion 36, and at least a part of the sides of the connection plate 33 and the sensing plate 32 is joined to the side of the sensor substrate 34, without the diaphragm 31 being directly joined to the sensor substrate 34. Thus, a resonating portion is formed of the diaphragm 31, the connection plate 33, the sensing plate 32, and the piezoelectric element 35, to form a mass sensor 30.

Here, although the diaphragm 31, the connection plate 33, and the sensing plate 32 are not necessarily required to have the same thickness, preferably they have the same thickness so as to form the same surface, and more preferably, they are integrally formed. The conditions related to the thickness and joining for the diaphragm 31, the connection plate 33, and the sensing plate 32 are likewise applied to all the mass sensors according to the present invention described below. Furthermore, the sides of the connection plate 33 and the sensing plate 32 are preferably formed integrally with the sensor substrate 34.

The structure of such a mass sensor 30 can be summarized to be a mass sensor having at least one piezoelectric element, in which a connection plate 33 and a diaphragm 31 are joined together at their respective sides; at least one sensing plate 32 is joined to the connection plate 33 at their respective side in the direction perpendicular to the direction where the diaphragm 31 is joined to the connection plate 33; and at least a part of the sides of the connection plate 33 and the sensing plate 32 is joined to a part of the sides of the sensor substrate 34. In the mass sensor 30, at least either one of oscillation modes can be utilized among the bending mode in which the diaphragm 31 oscillates as it bends in the direction of Z-axis (not shown) perpendicular to both X and Y axes; the axial rotation mode in which it oscillates as it rotates around the Y-axis; the θ-mode in which the diaphragm 31 performs pendulum-like oscillation centered on the Y-axis within the plate surface of the diaphragm 31 in the X-axis direction so as to make a constant angle θ to the Y-axis; and the φ-mode which is pendulum-like oscillation centered on the Y-axis in the X-axis direction, and in which the swing component in the direction of the Z-axis (not shown) parallel to the side of the diaphragm 31 is increased as it travels apart from the Y-axis.

Here, the above θ-mode and the φ-mode will be described in further detail. FIG. 5(b) is a diagram illustrating the θ-mode, and shows change in the location of the diaphragm 31 when the mass sensor 30 of FIG. 5(a) is viewed from the A—A direction in FIG. 5(a), that is on the X-axis from the Y-axis direction. Here, the upper end surface 31F of the diaphragm 31 is on the location P1 when not oscillating, but in the θ-mode, the diaphragm 31 performs pendulum-like oscillation centered on the Y-axis within the plate surface of the diaphragm 31, that is, in the X-Y axis plane in the X-axis direction so as to make a constant angle θ to the Y-axis. At this time, in the A—A direction, the movement of the upper end surface 31F of the diaphragm 31 can be described as the reciprocal movement between locations P2 and P3 on the X-axis, and this oscillating movement is defined as the θ-mode.

Next, FIG. 5(c) is a diagram illustrating the φ-mode, and similar to FIG. 5(b), FIG. 5(c) shows change in the location of the diaphragm 31 viewed from the A—A direction shown in FIG. 5(a). Here also, the upper end surface 31F of the diaphragm 31 is on the location P1 when not oscillating. As described above, in the φ-mode, the diaphragm 31 performs pendulum-like oscillation centered on the Y-axis within the surface of the diaphragm 31 in the X-axis direction, and the swing component in the direction of the Z-axis parallel to the side of the diaphragm 31 is increased as it travels apart from the Y-axis. That is, the movement of the upper end surface 31F of the diaphragm 31 in the A—A direction can be described as the reciprocal movement between locations P4 and P5 on the arc orbit S having the center O at a point of the Z-axis and passing through location P1. At this time, the angle made by the Z-axis and the straight line connecting the diaphragm 31 and the center O is φ, and such an oscillation mode is defined as the φ-mode.

Due to these various modes of oscillation, the piezoelectric film of the piezoelectric element 35 is subjected to stretching stress or flexural stress, and a voltage corresponding to the magnitude of the stress is generated. The resonant frequency of the resonating portion comprising the diaphragm 31, the connection plate 33, and the sensing portion 36 at this time is measured by the piezoelectric element 35. Now, since the resonant frequency of the resonating portion varies mainly accompanying change in the mass of the diaphragm 31, when some substance attaches to, or detaches from the diaphragm 31 to cause the mass of the diaphragm 31 to change, the change in the mass can be obtained from change in the resonant frequencies of the resonating portion in the same principle as mass sensors 50A through 50D. The dynamic range can be increased by installing two piezoelectric elements 35 on both surfaces of the sensing plate 32, and by the comparison operation of the signals sensed by these piezoelectric elements 35. Furthermore, in this case, sensitivity can be improved by using one of the piezoelectric elements 35 for driving (exciting) the diaphragm 31, and the other for sensing (oscillation receiving).

Further in FIG. 5(a), it is preferable to improve sensitivity, to install one piezoelectric element 35 in the Y-axis direction split it into two piezoelectric element parts 35A and 35B, and use these for driving and sensing, respectively. The methods for splitting the piezoelectric element 35 include a method in which after installing one piezoelectric element 35, it is split by laser processing, and a method to install two piezoelectric element parts 35A and 35B respectively in the same time. These methods for installing a plurality of piezoelectric elements, and for splitting and using respective piezoelectric elements 35 can be applied to all the mass sensors according to the present invention.

Now, when a resonant frequency is measured by immersing the diaphragm 31 in a liquid utilizing the bending mode described above, the diaphragm 31 has a disadvantage that the diaphragm 31 receives resistance from the liquid corresponding to the area of the diaphragm 31, and becomes difficult to sense change in the minute mass of the diaphragm 31. However, when the specimen is gas, the bending mode can be used because the resistance value is small. In this case, however, it is preferable to shorten the length of the diaphragm 31 in Y-axis and X-axis directions.

Figure 6:
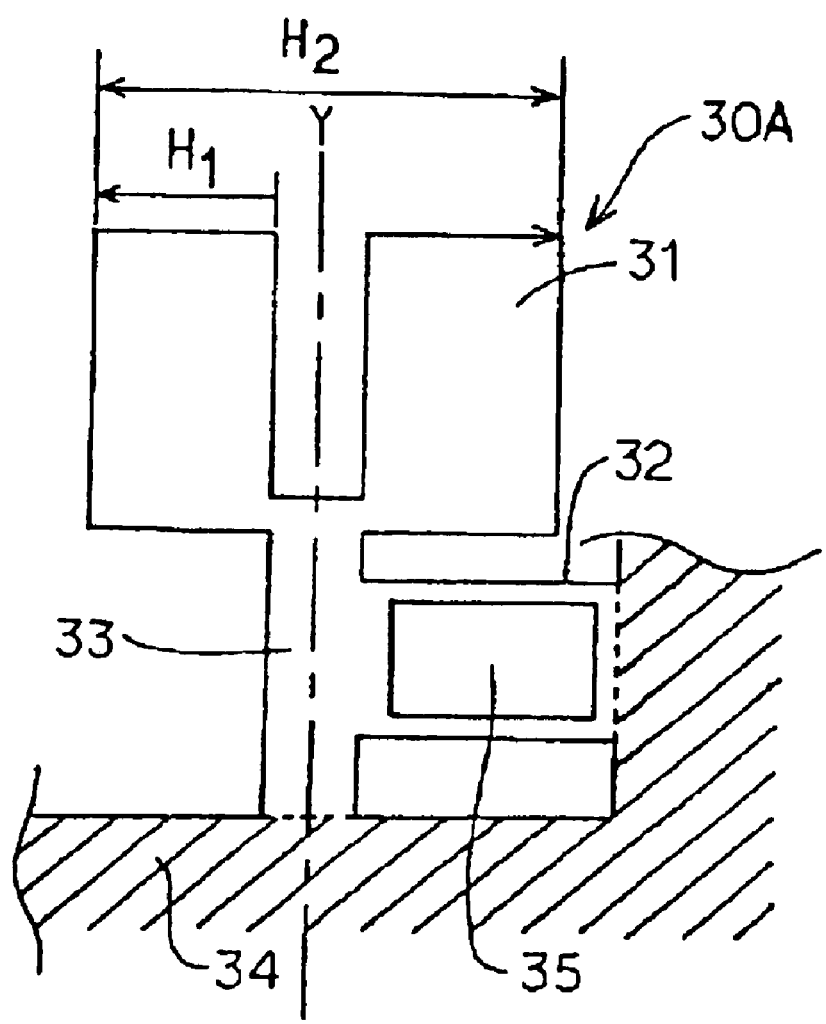
FIG. 6 is a plan showing still another embodiment of a mass sensor of the present invention.

In the rotation mode around the Y-axis, since change in the mass of the diaphragm 31 where the width of the connection plate 33 (width in the X-axis direction) is extended toward the diaphragm 31, in the vicinity of the Y-axis little affects the rotational oscillation of the diaphragm 31, and less contributes to the rotational oscillation than the same change in mass at the left and right ends of the diaphragm 31, a problem arises in sensitivity depending on the location where change in mass of the diaphragm 31 occurs. In this case, measurement error can be minimized by making the shape of the diaphragm 31 concave, and making the area in the vicinity of the Y-axis small like the mass sensor 30A in FIG. 6. At this time, in order to minimize measurement error at the location of applying the specimen when change in mass is same, it is preferable to decrease the dimension $H_1$; in order to raise the dynamic range, it is preferable to increase the dimension $H_2$.

Whereas, when the θ-mode or the φ-mode is used, no matter which the specimen is, liquid or gas, the effect of the location where the catching substance is applied to the diaphragm 31 can be minimized by decreasing dimensions $H_3$ and $H_4$ in FIG. 5. In addition, since the diaphragm 31 is thin, the effect of density or viscosity is small, and since the diaphragm 31 is operated in a rigid body mode, it is little affected by temperature change, making the mass sensor excel in sensitivity and environment resistance. Therefore, it is preferable to operate the mass sensor of the present invention in the θ-mode or the φ-mode.

Next, in the present invention, a structure in which a spring plate is bonded in one plate surface or either surface of the connection plate, and the spring plate is joined to a sensor substrate or a spring plate reinforcement can also be adopted favorably. FIG. 7(a) is a plan view showing the mass sensor 40A, which is an embodiment in which a spring plate 38 and a spring plate reinforcement 39 are installed on the mass sensor 30 described above. FIGS. 7(b) through (e) are various sectional views on the Y axis viewed from the X-axis direction, showing examples of the installation of the spring plate 38 and the spring plate reinforcement 39.

The spring plate 38 is joined to at least one plate surface of the connection plate 33. Although the width of the spring plate 38 may be narrower than the width of the connection plate 33 as FIG. 7(a) shows, it is preferable that the width of the spring plate 38 is the same as the width of the connection plate 33. Also, when spring plates 38 made of the same material are bonded on both plate surfaces of the connection plate 33, it is preferable that the shapes of these spring plates 38 are the same. However, when the materials of the spring plates 38 are changed on different materials of the connection plate 33, the shapes of these spring plates 38 are not required to be the same, but suitable shapes may be adopted considering the Young's modulus or other physical properties of each spring plate 38.

Such spring plates 38 are joined also to the sensor substrate 34 as a rule. In this case, the necessity of the spring plate reinforcement 39 is determined depending on the location where the connection plate 33 is joined to the sensor substrate 34. That is, when the connection plate 33 is joined to the location where the spring plate 38 is directly joined to the sensor substrate 34 as shown in FIGS. 7(b) and (c), no spring plate reinforcement 39 is required, because the sensor substrate 34 also functions as the spring plate reinforcement 39. At this time, the spring plate 38 may be bonded only on one plate surface of the connection plate 33.

However, when the connection plate 33 is joined to the sensor substrate 34 at its end as FIG. 7(d) shows, for the spring plate 38A, the sensor substrate 34 also functions as the spring plate reinforcement 39; however, for the spring plate 38B, it is preferable to provide a spring plate reinforcement 39 for supporting the spring plate 38B. Even when the connection plate 33 is joined to the sensor substrate 12 at its end as FIG. 7(e) shows, no spring plate reinforcement 39 is required if only the spring plate 38A which can be joined to the sensor substrate 12 is bonded, and no spring plate 38B is used.

Thus, by bonding the spring plate 38, the mechanical strength of the resonating portion is enhanced. Also, by this, the thickness of the connection plate 33 and the diaphragm 31 can be decreased, and the attenuation of the resonance peak on measurement in a liquid is advantageously reduced. Furthermore, it is preferable to bond spring plates 38 on both plate surfaces of the connection plate 33 because the center of gravity of the spring portion consisting of the connection plate 33 and the spring plates 38 can be excited, and the diaphragm 31 oscillates easily in the θ-mode, when exciting the diaphragm 31 with the piezoelectric element 35.

Figure 8A:
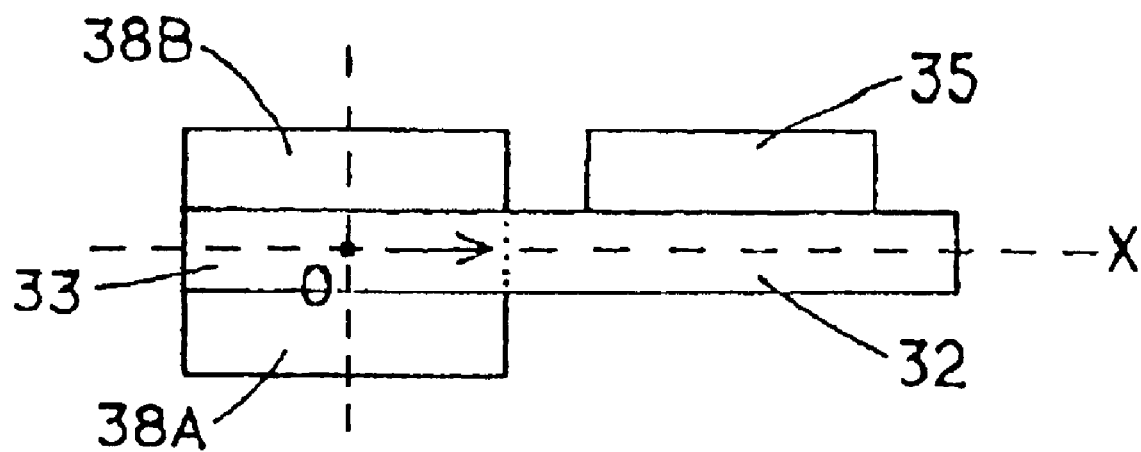
FIGS. 8(a)–(b) are diagrams illustrating the driving of a mass sensor of the present invention.
Figure 8B:
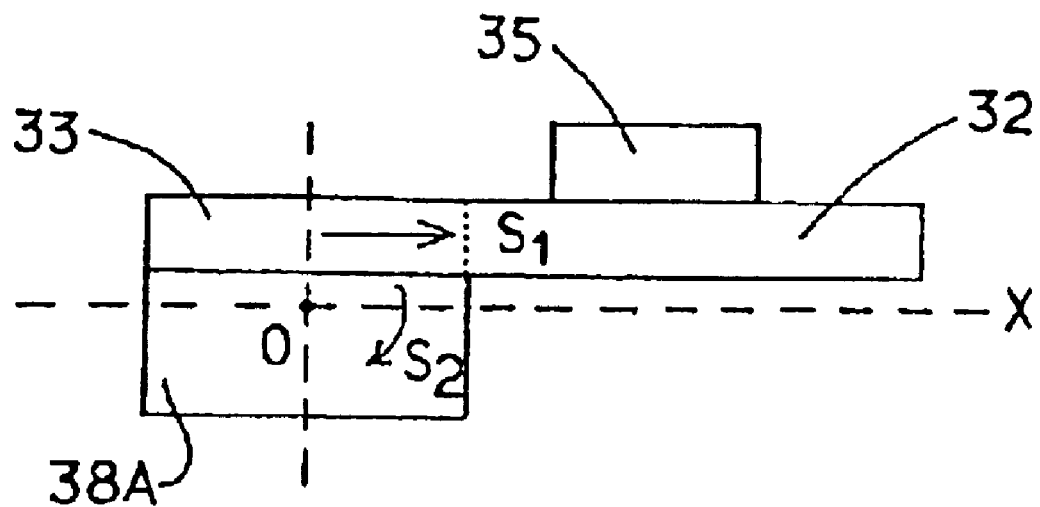

Here, sectional views on the X-axis viewed from the Y-axis direction of the embodiments shown in FIGS. 7(c) and (d) are shown in FIGS. 8(a) and (b), respectively. In FIG. 8(a), since the piezoelectric element 35 can drive the center O of the spring plate 38A, the spring plate 38B, and the connection plate 33 in the X-axis direction, the diaphragm 31 and the whole resonating portion oscillate easily in the θ-mode in the X-axis direction. Whereas, in the case of FIG. 8(b), since the center O of the spring plate 38A, the spring plate 38B, and the connection plate 33 is not on the connection plate 33, the driving force in the X-axis direction (arrow $S_1$) by the piezoelectric element 35 is exerted as a rotational force around the center O (arrow $S_2$) and the rotation mode appears easily, even though the rotation mode is restricted by the rigidity of the spring plate 38A itself.

Figure 9A:
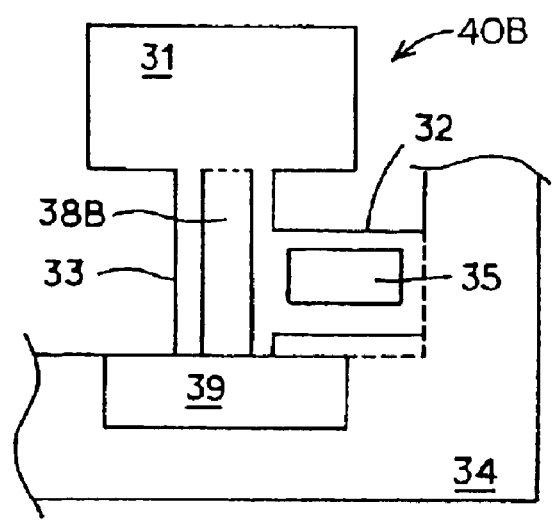
FIGS. 9(a)–(c) are diagrams showing still another embodiment of a mass sensor of the present invention; (a) and (b) are plans; and (c) is a sectional view.
Figure 9B:
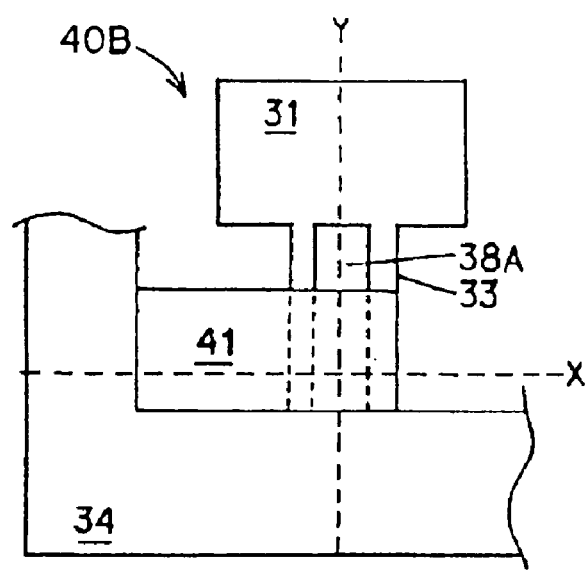
Figure 9C:
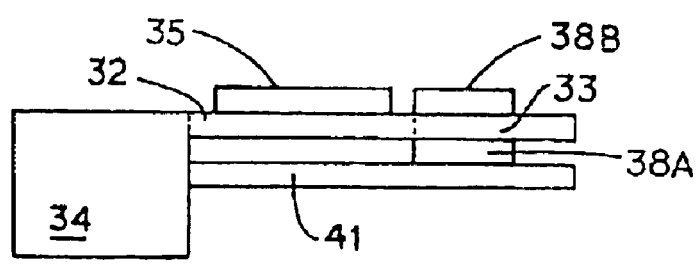

When the spring plate 38 is used as described above, it is also preferable that a reinforcing plate 41 is bonded to the spring plate 38 and joined to the side of the sensor substrate 34, as shown in the mass sensor 40B of FIG. 9. FIGS. 9(a) and (b) are plans of the mass sensor 40B viewed from the top and the bottom, respectively; and FIG. 9(c) is a sectional view along the X-axis viewed from the Y-axis direction in FIG. 9(b). Here, the reinforcing plate 41 is bonded to the spring plate 38A installed on the connection plate 33, and joined to the sensor substrate 34 at the perpendicularly cut side. Preferably, the reinforcing plate 41 is integrally formed with the spring plate 38 and the sensor substrate 34.

Since such a structure facilitates the diaphragm 31 to resonate in the θ-mode and the φ-mode, the attenuation of the Q value is reduced, and sensitivity is advantageously improved. Therefore, the structure is suitable particularly for measurement in liquid.

Obviously, the spring plate described above can be applied to all the mass sensors according to the present invention in which a connection plate is used as a component, and it is preferable that the spring plate is integrally formed with an intermediate plate integrally inserted between the diaphragm plate and the base plate, or integrally formed with a spring plate reinforcement which has been integrally formed with the diaphragm, and also integrally formed with respective connection plates as described later in the method for manufacturing the mass sensor of the present invention.

Figure 10A:
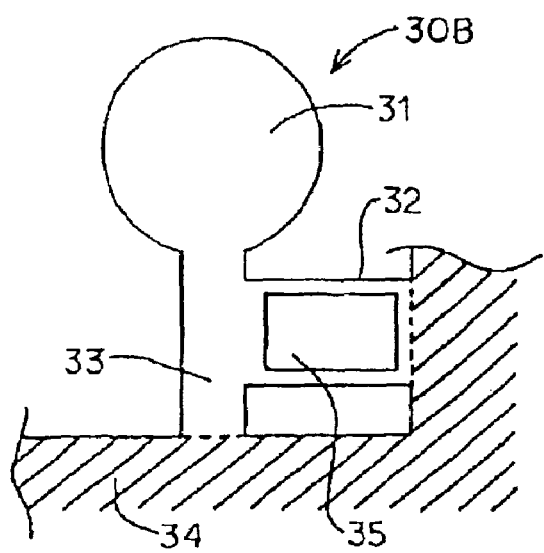
FIGS. 10(a)–(d) are plan views showing still another embodiment of a mass sensor of the present invention.
Figure 10B:
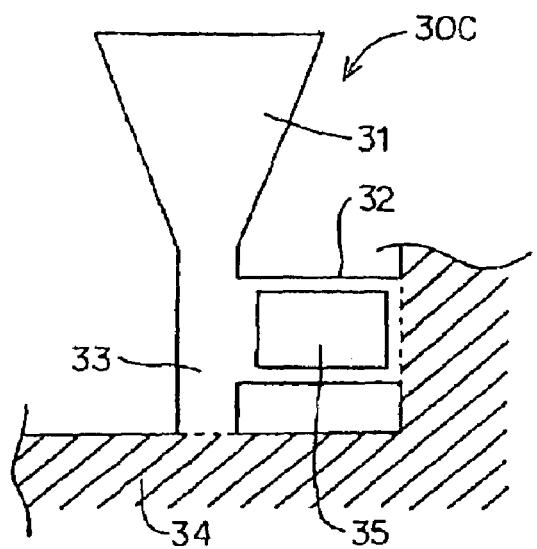
Figure 10C:
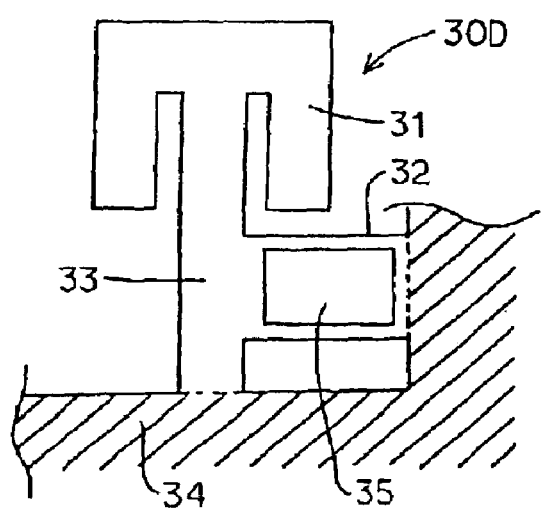
Figure 10D:
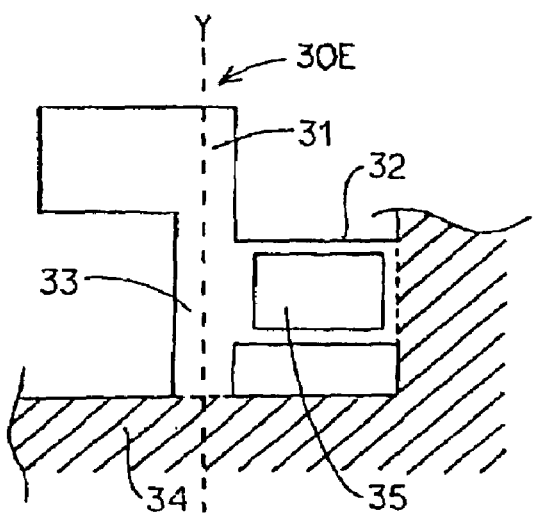

The shape of the plate surface of the diaphragm 31 in the above mass sensor 30 is not limited to rectangular as shown in FIG. 5(a), FIG. 7(a), and FIG. 9, but various optional shapes, such as circular, triangular, inverted U-shape, polygonal, ellipse, and oval, as shown in mass sensors 30B through 30D of FIGS. 10(a) through (c), may be used. The diaphragm 31 may be not joined to the connection plate 33 symmetrically about the Y-axis, as shown in the mass sensor 30E of FIG. 10(d). Such an optional selection of the shape of the diaphragm 31 can also be applied to all the mass sensors of the present invention.

Figure 11:
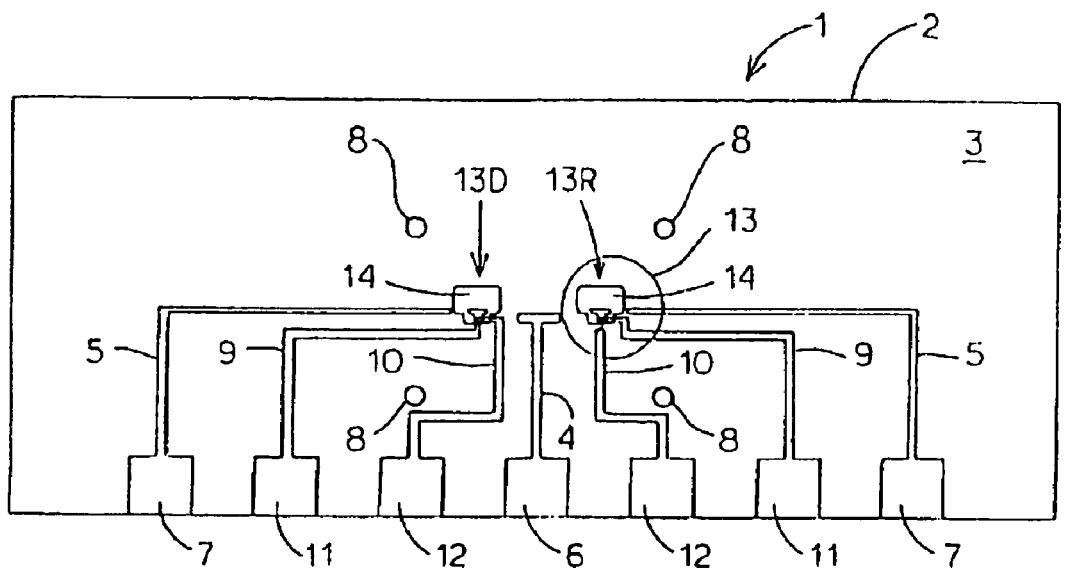
FIG. 11 is a plan showing the appearance of still another embodiment of a mass sensor of the present invention.

Next, an embodiment of a mass sensor in which only one spring plate is bonded to the mass sensor 30 described above, and is assembled in the sensor substrate is shown in FIG. 11. In the mass sensor 1, it is obviously possible to form the spring plate, spring plate reinforcement, and reinforcing plate described above, or to change the shape of the diaphragm optionally.

FIG. 11 is a plan of a mass sensor 1 viewed from the direction of the diaphragm 3. The mass sensor 1 is designed to be symmetrical. The oscillation plate 3 constitutes the sensor substrate 2 together with the base plate 15 and the intermediate plate 17 as described later. Holes 8 formed in the sensor substrate 2 are used as alignment marks utilized in packaging and manufacturing processes of the mass sensor 1, and two resonating portions 26, one of which is used for referencing, consisting of a diaphragm 19, a connection plate 20, a sensing plate 21, a piezoelectric element 25, and a spring plate 18 as described later are formed. By forming two or more resonating portions 26 in one mass sensor 1, including a resonating portion 26 for referencing, signals from respective resonating portions 26 can be cumulated to expand the dynamic range.

The position sensor electrodes 4, 5 are used for sensing the position of the mass sensor 1 when the mass sensor 1 is immersed in a conductive specimen such as an aqueous solution by conducting an electric current through the specimen. When the specimen is conductive, these position sensor electrodes 4, 5 prevent the second electrode 24 and the first electrode 22 on the piezoelectric element 25 (not shown in FIG. 11), and electrode leads 9, 10 from these electrodes from short-circuiting, by making the part above the pattern formed in the horizontal direction of the position sensor electrodes 4, 5 immersed in the specimen, and making the part of the mass sensor 1 deeper than the position the position sensor electrodes 4, 5 sensed not immersed in the specimen. To an end of each of the position sensor electrodes 4, 5 is formed a terminal 6, 7, respectively; and to an end of each of the electrode leads 9, 10 is formed a terminal 11, 12, respectively. These terminals are connected to the probes or other connectors on respective sensor instruments.

However, when the piezoelectric element 25 and the electrode leads 9, 10 are coated with an insulating resin or the like, since these piezoelectric element 25 and electrode leads 9, 10 are not short-circuited even if the mass sensor 1 is immersed in the conductive specimen, no position sensors 4, 5, and terminals 6, 7 are required.

Figure 12:
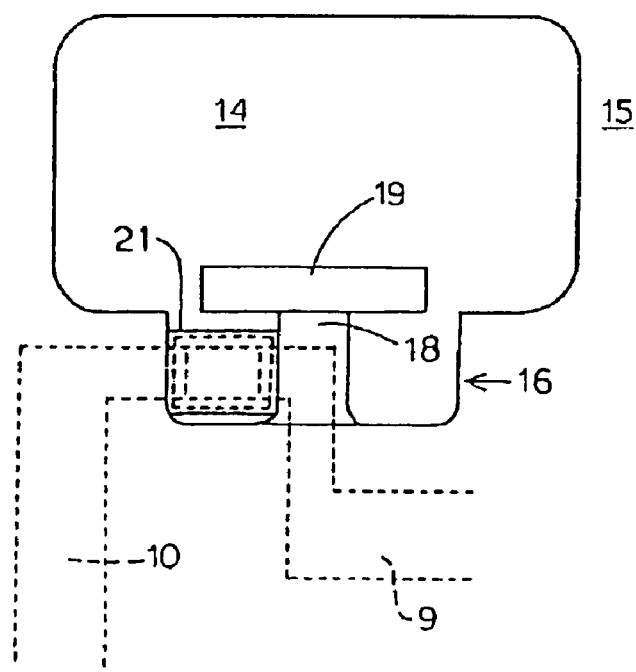
FIG. 12 is a plan showing the structure of the sensor portion in the mass sensor shown in FIG. 11.
Figure 13:
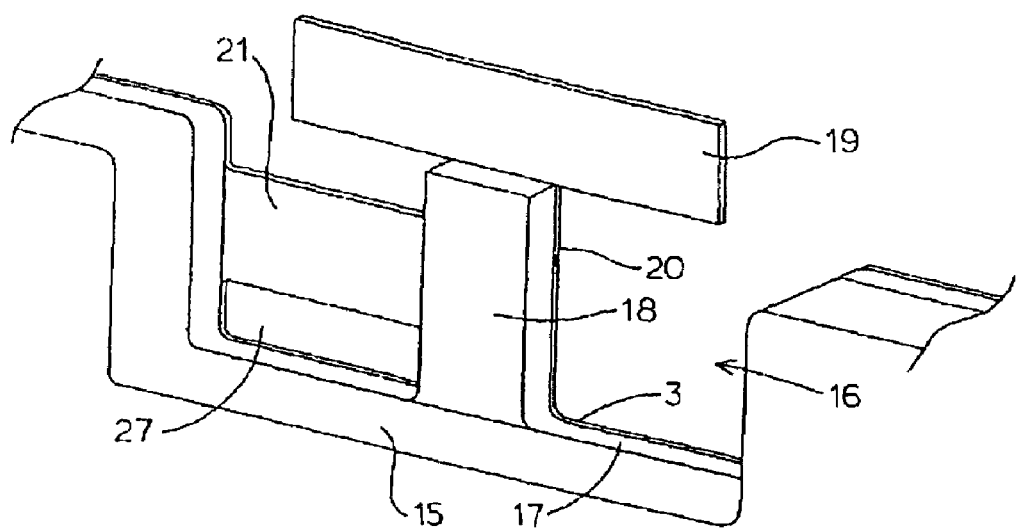
FIG. 13 is a perspective view showing the structure of the sensor portion in the mass sensor shown in FIG. 12.

FIG. 12 is an enlarged plan showing the sensor portion 13 in FIG. 11 viewed from the base plate 15, that is, viewed from the back side of the oscillation plate 3 in FIG. 11. FIG. 13 is a perspective view showing the vicinity of the cut portion 16 shown in FIG. 12. The sensor portion 13 means a portion of the mass sensor 1, comprising the resonating portion 26 and the sensor substrate 2 in the vicinity of the resonating portion 26 in the mass sensor 1.

As FIGS. 12 and 13 show, an opening 14 having U-shaped cut portion 16 is formed in the base plate 15. The same shape of cut portion 16 is also formed on the intermediate place 17 overlapping the base plate 15, and in the intermediate place 17, an almost prismatic spring plate 18 extending toward the center of the opening 14 from the center of the bottom side of the cut portion 16 is formed. However, these intermediate plate 17 and the spring plate 18 are not always required, but are used as the members constituting the mass sensor 1 when required for the adjustment of the mechanical strength of the resonating portion 26 or the sensitivity of the mass sensor 1.

In the cut portion 16 of the oscillation plate 3 are formed a connection plate 20 joined to the spring plate 18, and a diaphragm 19 joined to the upper end of the connection plate 20, but not joined to the spring plate 18. Furthermore, in the cut portion 16 of the oscillation plate 3, a sensing plate 21 is formed across a side of the connection plate 20 and the facing side of the cut portion 16.

Figure 14:
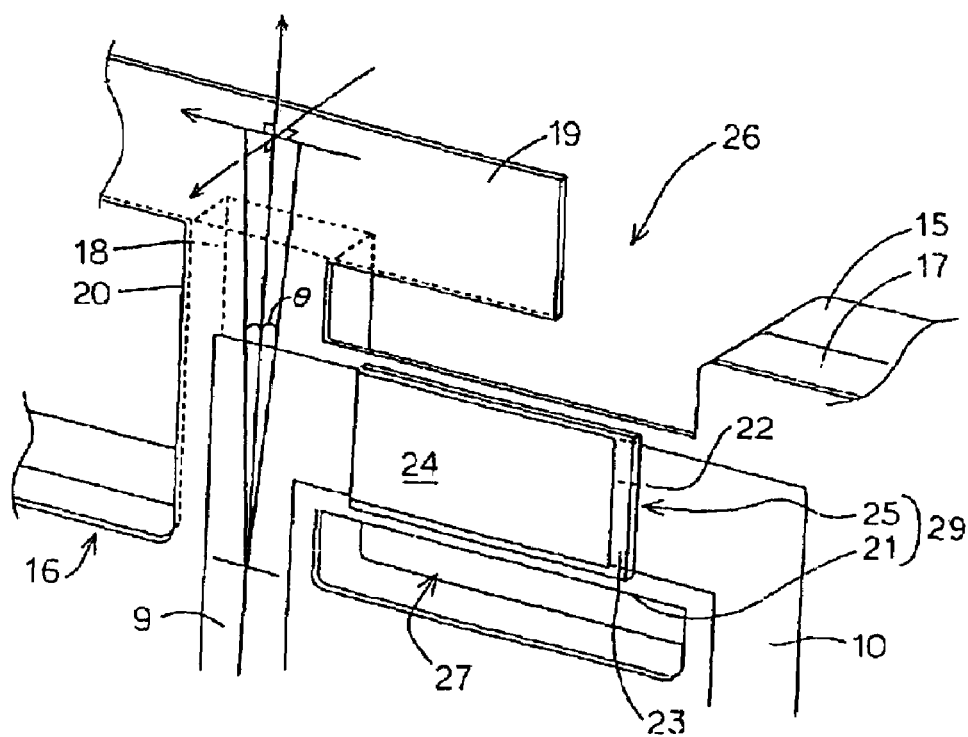
FIG. 14 is another perspective view showing the structure of the sensor portion in the mass sensor shown in FIG. 12.

FIG. 14 shows a perspective view of the vicinity of the cut portion 16 shown in FIG. 12 viewed from the oscillation plate 3 side. On the surface of the oscillation plate 3 side of the sensing plate 21 is formed a piezoelectric element 25 by laminating a first electrode 22, a piezoelectric film 23, and a second electrode 24 in this order. Furthermore, the second electrode 24 is connected to the electrode lead 9, and the first electrode 22 is connected to the electrode lead 10. Thus, a sensing portion 29 is constituted of the sensing plate 21 and the piezoelectric element 25, and the resonating portion 26 is constituted of the spring plate 18, the diaphragm 19, connection plate 20, and the sensing portion 29.

Although only a piezoelectric element 25 is installed on one plate surface of the sensing plate 21 in the mass sensor 1, piezoelectric elements 25 may be installed on both plate surfaces of the sensing plate 21. In this case, since the structure of the sensing portion 29 becomes symmetrical, the rigidity of the sensing plates 21 can be equalized.

Figure 15:
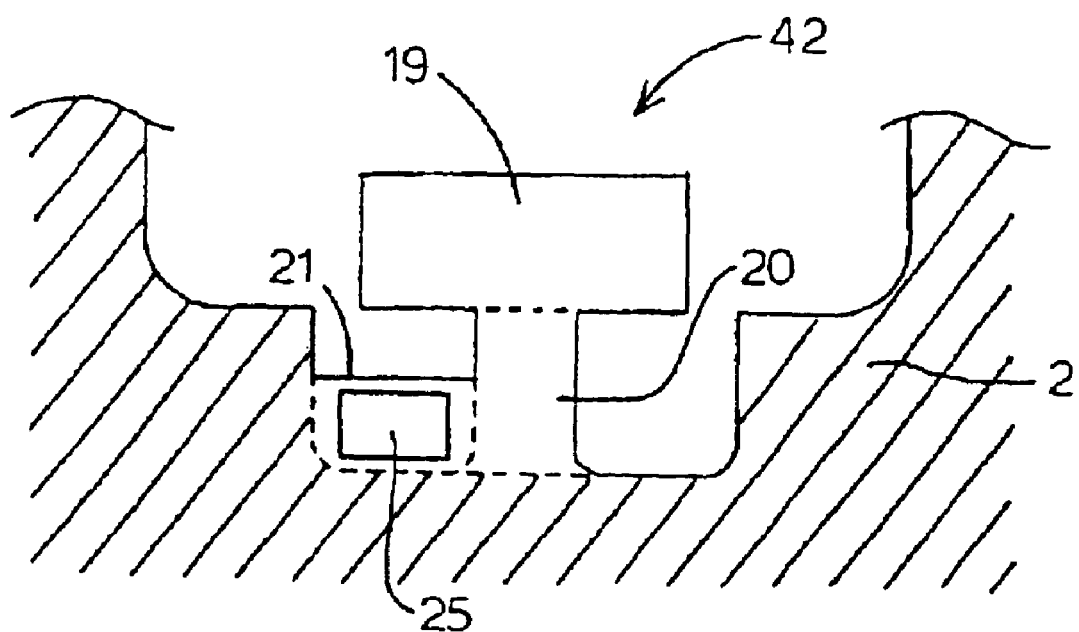
FIG. 15 is a plan showing still another embodiment of a mass sensor of the present invention.

Also in the mass sensor 1, although a slit 27 is formed on the lower edge of the cut portion 16 in the sensing plate 21 and the oscillation plate 3 as FIG. 13 shows, it is preferable that a structure in which the sensing plate 21 is joined to the lower edge of the cut portion 16 in the oscillation plate 3 without forming the slit 27, that is, the sensing plate 21 is fitted in and joined to the depression formed by the connection plate 20 and the sensor substrate 2 as in the mass sensor 42 shown in FIG. 15, to restrict the bend of the spring portion consisting of a connection plate 20 and/or a spring plate 18, and to increase the stress applied to the piezoelectric element 25.

In the mass sensor 1 described above, although a sensor portion 13 is installed utilizing the circumference of the opening 14 formed in the sensor substrate 2, the sensor portion 13 may be installed on the circumference of the sensor substrate 2, for example, on the upper edge in FIG. 11. However, since the sheet-like diaphragm 19 is often installed on the location projected from the cut portion 16, as obvious from the structure of the sensor portion 13 shown in FIGS. 11 through 14, it is preferable to adopt the structure in which the sensor portion 13 is installed inside the sensor substrate 2 as FIG. 11 shows, considering the protection of the resonating portion 26 from external impact, for example, so as not to damage the diaphragm 19 on handling the mass sensor 1. Such a structure is also preferable for facilitating the manufacturing process of the mass sensor 1 as will be described later.

Figure 16A:
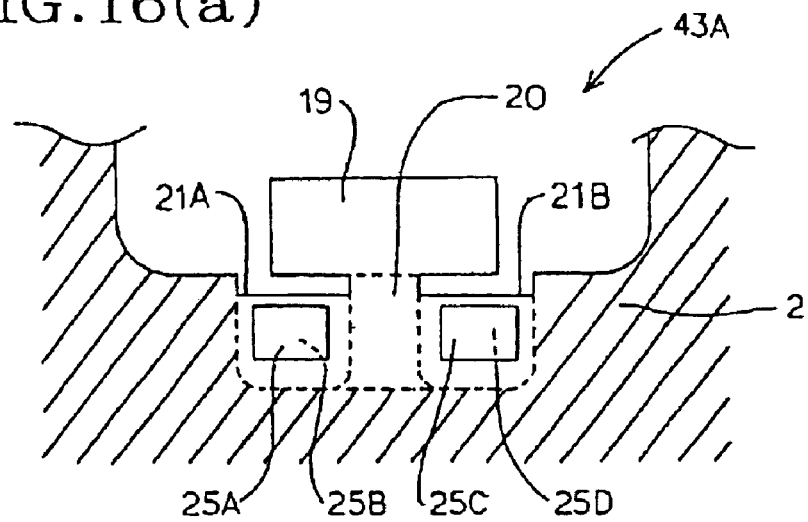
FIGS. 16(a)–(c) are plan views showing still another embodiment of a mass sensor of the present invention.
Figure 16B:
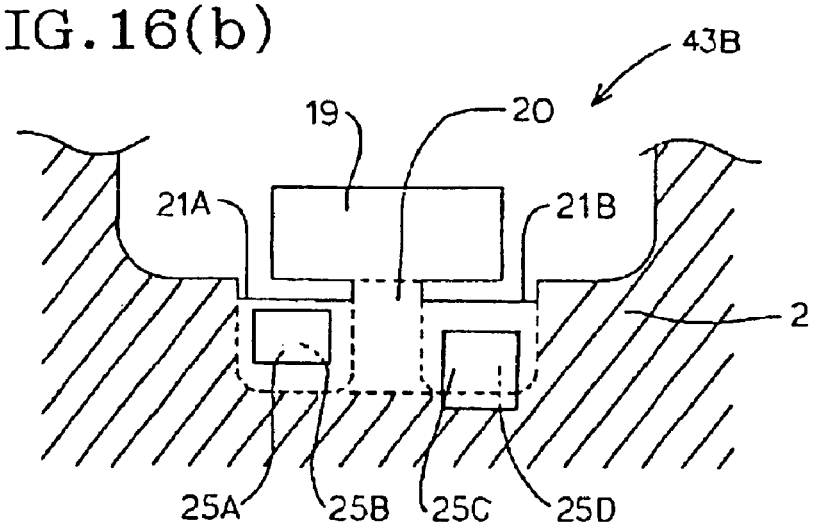

Next, various embodiments of mass sensors that can substitute the sensor portion 13 in the mass sensor 1 described above will be described. FIG. 16(*a*) is a plan showing a mass sensor 43A, which is another embodiment of the present invention. The mass sensor 43A has the structure in which a connection plate 20 and a diaphragm 19 are joined together at the respective sides, two sensing plates 21A, 21B are joined to the connection plate 20 so as to sandwich the connection plate 20 in the direction perpendicular to the direction where the diaphragm 19 and the connection plate 20 are joined, and respective sensing plates 21A, 21B are also joined to the sensor substrate 2 in the same way as the sensing plate 21 in the mass sensor 42 shown in FIG. 15 and supported and fixed at three sides. This three-side supporting is intended to elevate sensitivity. However, the sensing plates 21A, 21B are not necessarily required to be joined to the lower edge of the depression formed by the connection plate 20 and the sensor substrate 2.

Piezoelectric elements each consisting of a first electrode, a piezoelectric film, and a second electrode are installed on at least a part of at least one of the plate surfaces of at least one of the sensing plates. In the embodiments shown in FIG. 16, piezoelectric elements 25A through 25D are installed on both plate surfaces of sensing plates 21A, 21B, and the resonating portion is formed of a diaphragm 19, a connection plate 20, the sensing plates 21A, 21B, and the piezoelectric elements 25A through 25D. However, all the piezoelectric elements 25A through 25D are not necessarily required, but the optional number of the piezoelectric elements may be installed on optional locations of the sensing plate 21A or 21B.

When a plurality of piezoelectric elements 25A through 25D are used as in this mass sensor 43A, since the rigidity of the sensing plates 21A and 21B can be equalized, and in addition, the Q values in the $\theta$-mode and the $\phi$-mode can be increased and the Q value of the rotation mode can be decreased by cumulating or processing signals from the respective piezoelectric elements 25A through 25D, resonant frequencies can be measured more accurately. Furthermore, when at least two of the piezoelectric elements 25A through 25D are installed, if one is used for driving and the other is used for sensing, sensitivity can be improved. Here, it is preferable for improving sensitivity to split these piezoelectric elements 25A through 25D in the similar way as the piezoelectric element 35 is split into piezoelectric elements 35A and 35B in the mass sensor 30.

It is also preferable for improving output charge to adopt the structure in which, for example, piezoelectric elements 25A and 25C are installed on the plate surfaces in the same orientation of sensing plates 21A and 21B, respectively, and the polarizing direction of the piezoelectric films in these piezoelectric elements 25A and 25C is reversed to each other. It is also preferable to adopt such a structure on respective plate surfaces of the sensing plates 21A and 21B. Furthermore, it is preferable for improving sensitivity to adopt the structure in which at least one of directions of at least one of the piezoelectric elements 25A through 25D, for example, the piezoelectric elements 25C and 25D is a side or two sides of three-side supporting as in the mass sensor 43B shown in FIG. 16(*b*). Even in this case, however, it is required that the piezoelectric elements 25A through 25D do not overlap the spring plate when the connection plate 20 and the spring plate are used.

When spring plates are bonded to mass sensors 43A, 43B, spring plate reinforcements or reinforcing plates can be used as in the mass sensor 40B. For example, a reinforcing plate is formed so that it is bonded to a spring plate, and the side of the reinforcing plate is joined to three sides, that is, the sides of the sensor substrate 2 where the sensing plates 21A, 21B, are joined to the sensor substrate 2 (the lateral side of the cut portion 16), and the side of the sensor substrate 2 where the connection plate 20 is joined to the sensor substrate 2 (the bottom side of the cut portion 16). This is preferable for improving sensitivity, because the Q value in the θ-mode can be improved, the resonant frequency in the flexural mode (the mode bending between the sensor substrate and the connection plate) of the piezoelectric element can be increased, and the frequency in the θ-mode can be increased.

The mass sensor 43C shown in FIG. 16(*c*) is an embodiment in which a slit 48 is formed on the center in the length direction of the connection plate 20 in the mass sensor 43A. The slit 48 is hollow, and has functions to facilitate oscillation in the θ-mode and the φ-mode of the diaphragm 19 to occur, and the resonant frequency to be identified. Also, as described later, the slit 48 has functions to reduce the mass of the connection plate 20 and to improve sensitivity. When a spring plate is used, the spring plate may be formed in the shape having such a hollow, and integrated with the connection plate.

Figure 16C:
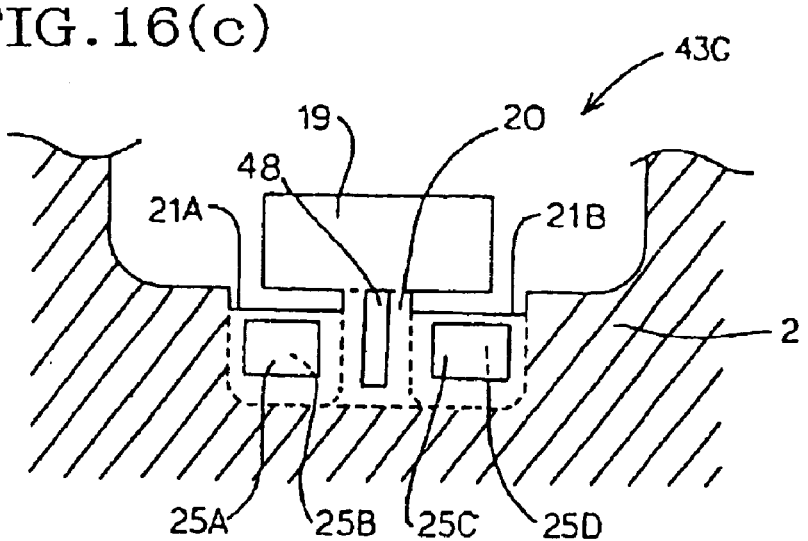
Figure 17A:
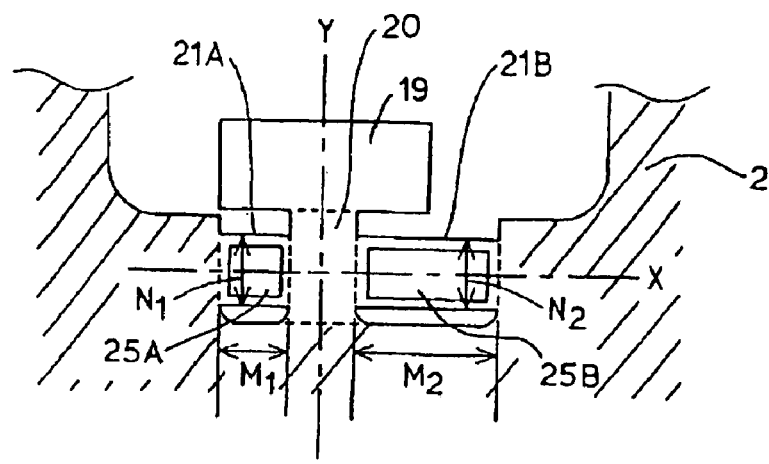
FIGS. 17(a)–(b) are diagrams showing still another embodiment of a mass sensor of the present invention; (a) is a plan; and (b) is a sectional view.
Figure 17B:
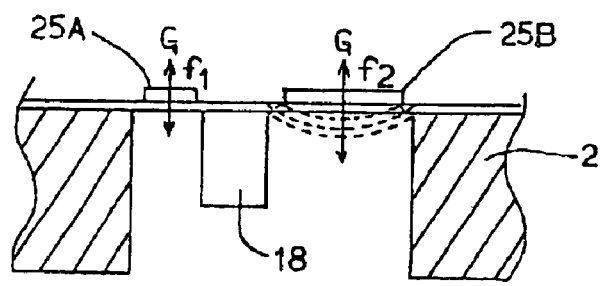

When two sensing plates are installed on one resonating portion as shown in FIG. 16(*a*), the driving force of the diaphragm 19 can be increased by expanding the area of either one of the sensing plates 21A and 21B by changing the lengths $N_1$ and $N_2$ and the widths $M_1$ and $M_2$ of the sensing plates 21A and 21B, and the Q values in the θ-mode and the φ-mode can be increased by narrowing the area of the other sensing plate, as FIG. 17(*a*) shows. FIG. 17(*b*) is a sectional view along the X-axis of FIG. 17(*a*) viewed from the Y-axis direction. The Q values in the θ-mode and the φ-mode can be increased or sensitivity is improved by changing the natural frequency of the bending displacement oscillation of the sensing plates 21A, 21B determined by the piezoelectric elements 25A, 25B and the sensing plates 21A, 21B (arrow G in FIG. 17(*b*)) to $f_1$ and $f_2$, respectively, by changing the widths $M_1$ and $M_2$ of the sensing plates 21A, 21B, for example, by using one of the piezoelectric elements 25A, 25B for driving and the other for sensing. Also, the piezoelectric element having either smaller natural frequencies $f_1$ and $f_2$ may be used for driving, and the other may be used for failure diagnosing.

Figure 18:
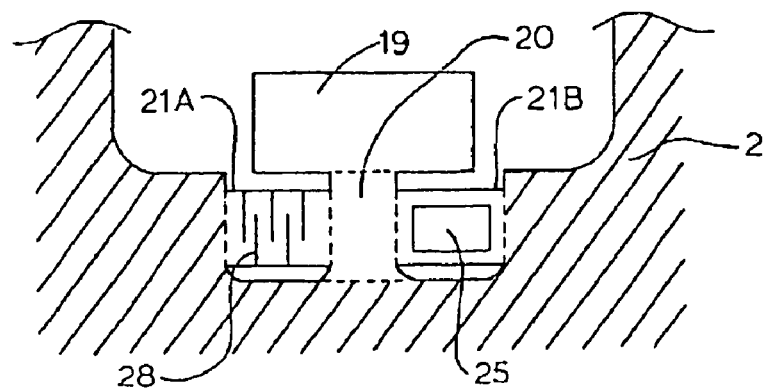
FIG. 18 is a plan showing still another embodiment of a mass sensor of the present invention.
Figure 19A:
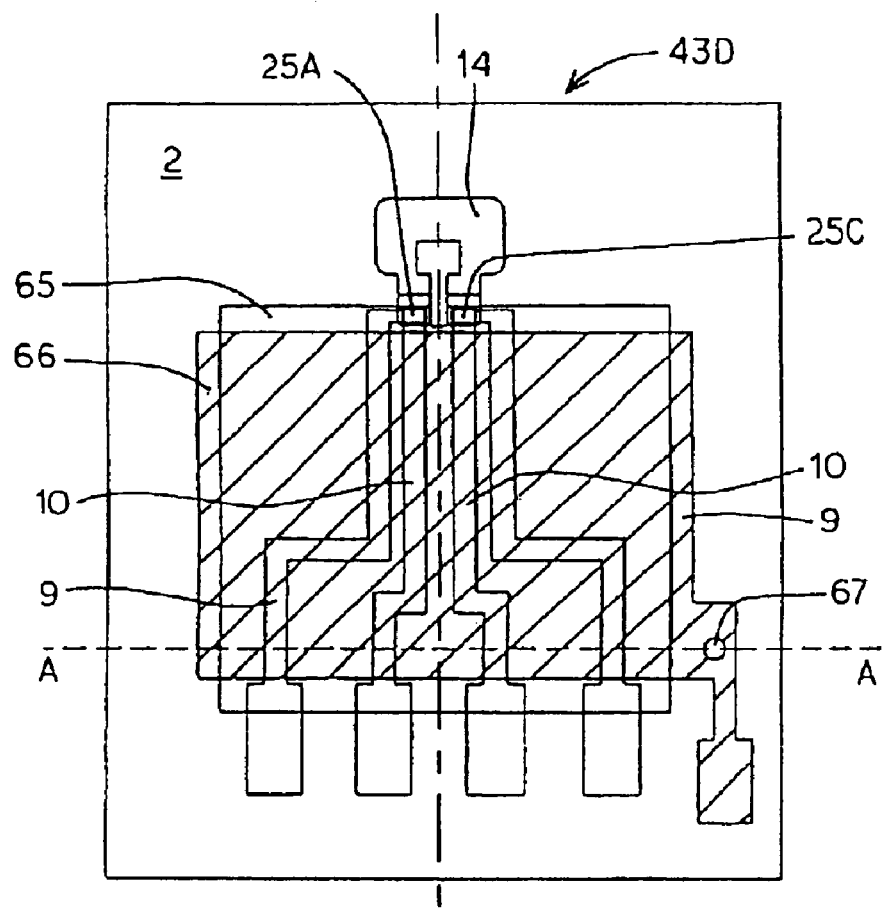
FIGS. 19(a)–(d) are diagrams showing still another embodiment of a mass sensor of the present invention; (a) is a plan; and (b) through (d) are sectional views.
Figure 19B:
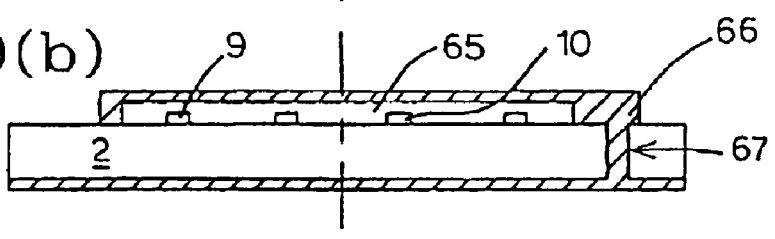
Figure 19C:
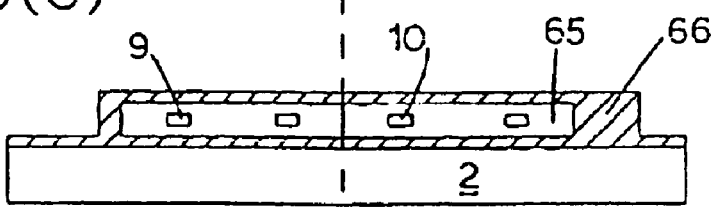
Figure 19D:
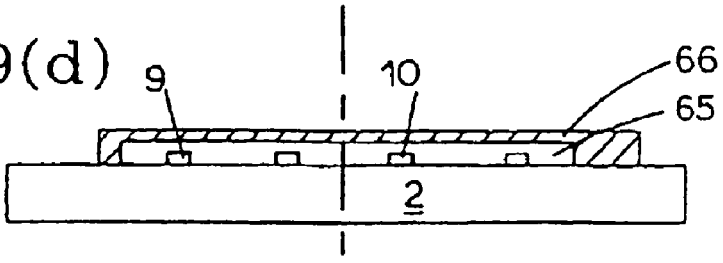

When two sensing plates are used in one resonating portion as shown in FIG. 16 or 17, it is also preferable to adopt a structure in which at least one of the piezoelectric elements 25C, 25D is installed on one sensing plate, for example, the sensing plate 21B, and a slit 28 is formed on the other sensing plate 21A in the direction perpendicular to the direction where the sensing plate 21A is joined to the connection plate 20 as FIG. 18 shows. By such a structure, the oscillation in the rotation mode can be restricted, the Q values in the θ-mode and the φ-mode can be increased, and the deviation of the resonance point can be increased to increase the absolute value of the variation of resonant frequencies. Although the number of the slit 28 may be one, a plurality of slits are preferable to enhance the effects mentioned above.

Next, FIG. 19(*a*) shows a plan of a mass sensor 43D, an embodiment in which the mass sensor 43A shown in FIG. 16(*a*) is formed in the opening 14 formed in the sensor substrate 2; FIG. 19(*b*) shows a sectional view thereof along the broken line A—A in FIG. 19(*a*). In the mass sensor 43D, two piezoelectric elements 25A, 25C are installed, and electrode leads 9, 10 are connected to the piezoelectric elements 25A, 25C, respectively. An insulation coating layer 65 is formed to cover the piezoelectric elements 25A, 25C and the electrode leads 9, 10. This insulation coating layer 65 protects the piezoelectric elements 25A, 25C and the electrode leads 9, 10 from short-circuiting even if the resonating portion of the mass sensor 43D is immersed in a conductive specimen.

The mass sensor 43D is also provided with shield layers 66 comprising a conductive material so as to cover the insulation coating layer 65. The shield layer 66 are formed on both the surfaces of the sensor substrate 2 and connected to each other through a through-hole 67. When sensing an extremely small mass of the 0.1 ng order, it is preferable to also shield the wiring members (piezoelectric elements 25A, 25C and electrode leads 9, 10) on the sensor substrate 2, as well as the wiring from the sensor substrate 2 to the instrument, in order to shield the mass sensor from external electromagnetic waves and to minimize the determination error of resonant frequencies.

In addition to the aspect of the formation of the shield layer 66 so as to sandwich the sensor substrate 2 as shown in FIG. 19(*b*), the embodiment in which the shield layer surrounds only the wiring members on the sensor substrate 2 as shown in the sectional view of FIG. 19(*c*), and the embodiment in which a shield layer covers only the upper side of the wiring members as shown in FIG. 19(*d*) may also be used. Particularly, the embodiments to shield the entire wiring members as shown in FIGS. 19(*b*) and (*c*) are preferable. In the embodiment of FIG. 19(*a*), although the shield layer 66 formed on both the surfaces of the sensor substrate 2 are electrically connected to each other through the through-hole 67, these layers may be connected by utilizing the side of the sensor substrate 2. The detail of the materials favorably used for the formation of the insulation coating layer 65 and the shield layer 66 will be described later together with the description of materials used in the mass sensors.

Figure 20A:
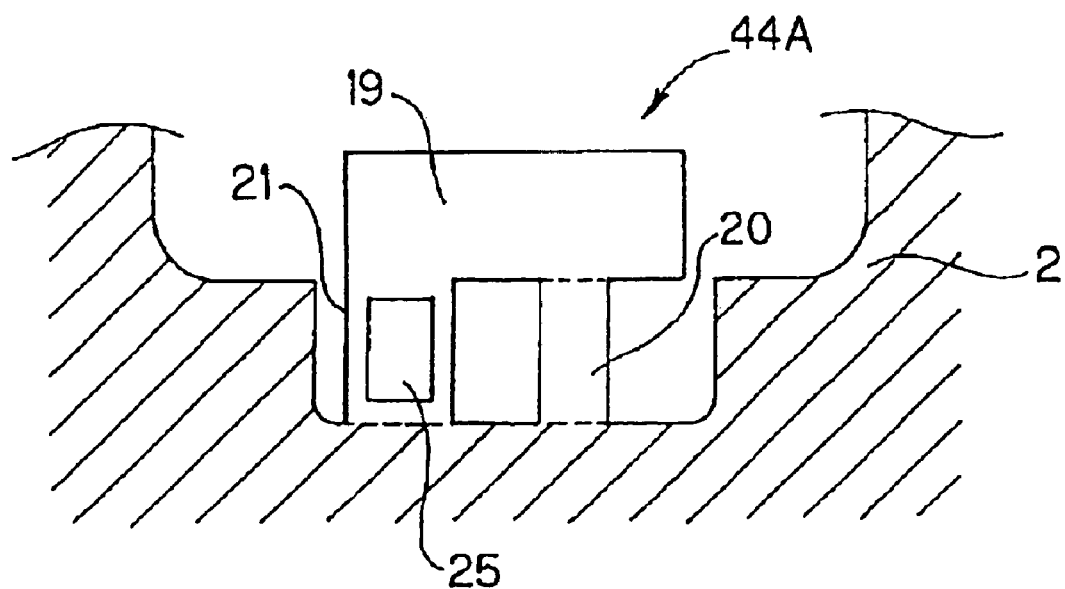
FIGS. 20(a)–(b) are plan views showing still another embodiment of a mass sensor of the present invention.
Figure 20B:
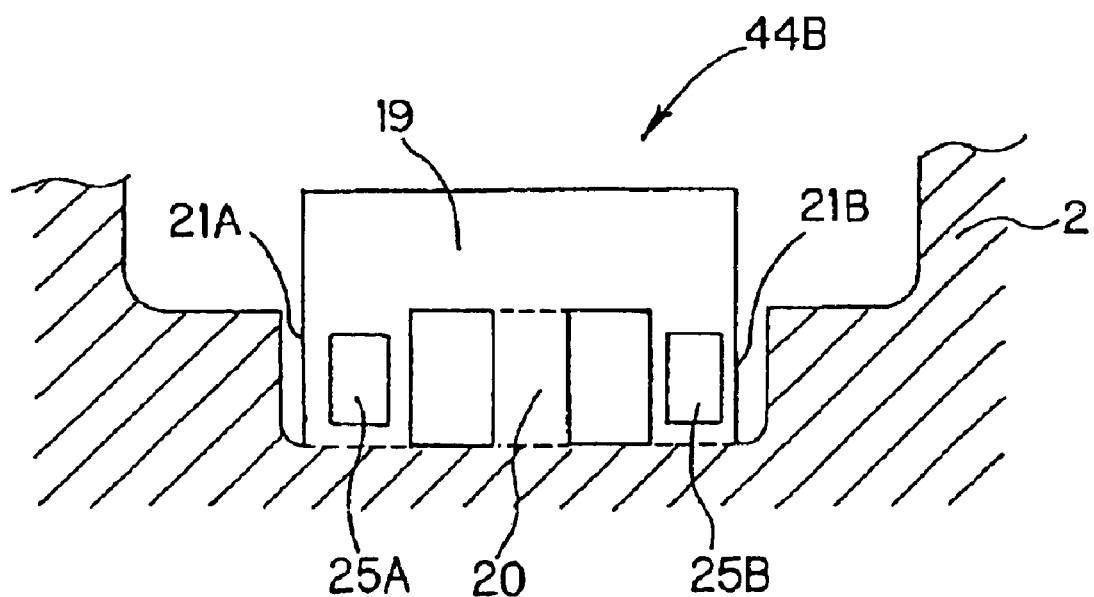

FIG. 20 is a plan view showing another embodiment of a mass sensor of the present invention. In the mass sensor 44A shown in FIG. 20(a), a connection plate 20 is not directly joined to a sensing plate 21, but the connection plate 20 and the sensing plate 21 are connected to a diaphragm 19 at respective sides so that the directions of joining to the diaphragm 19 are in parallel to each other, and the diaphragm 19 is not joined to the sensor substrate 2, but the connection plate 20 and the sensing plate 21 are connected to the side of the sensor substrate 2. That is, the sensing plate 21 also functions as the connection plate 20.

A piezoelectric element 25 is installed on at least a part of at least one of the plate surfaces of the sensing plate 21, and the resonating portion is formed of the diaphragm 19, the connection plate 20, the sensing plate 21, and the piezoelectric element 25. Whereas, in the mass sensor 44B shown in FIG. 20(b), two sensing plates 21A, 21B are formed on both the sides of a connection plate 20, and piezoelectric elements 25A, 25B are installed on the sensing plates 21A, 21B, respectively.

Such mass sensors 44A, 44B are suitable for measurement in the θ-mode, because the oscillation of the diaphragm 19 easily occurs in the plane of the diaphragm 19, and the oscillation of the diaphragm 19 in the rotation mode is restricted. Since the oscillation of the diaphragm 19 is directly transmitted to the piezoelectric element 25 through the sensing plates, the sensitivity of the mass sensors is advantageously improved.

Figure 21A:
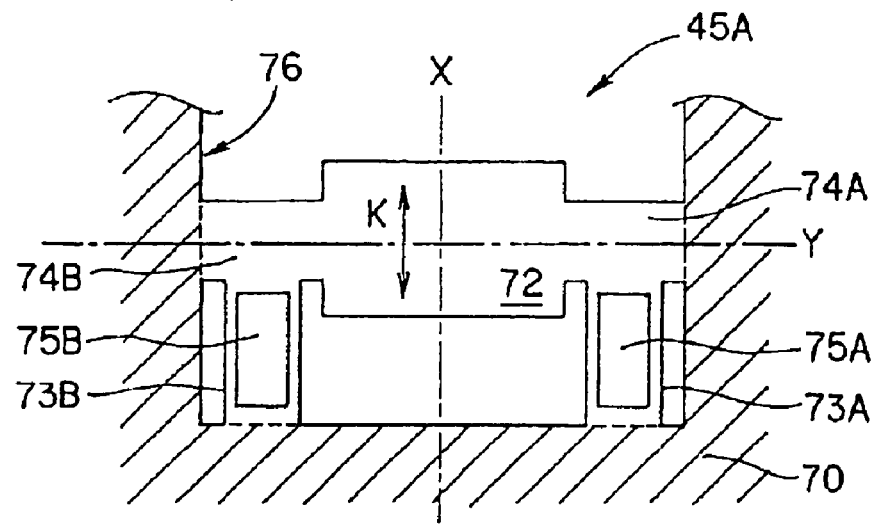
FIGS. 21(a)–(c) are plan views showing still another embodiment of a mass sensor of the present invention.
Figure 21B:
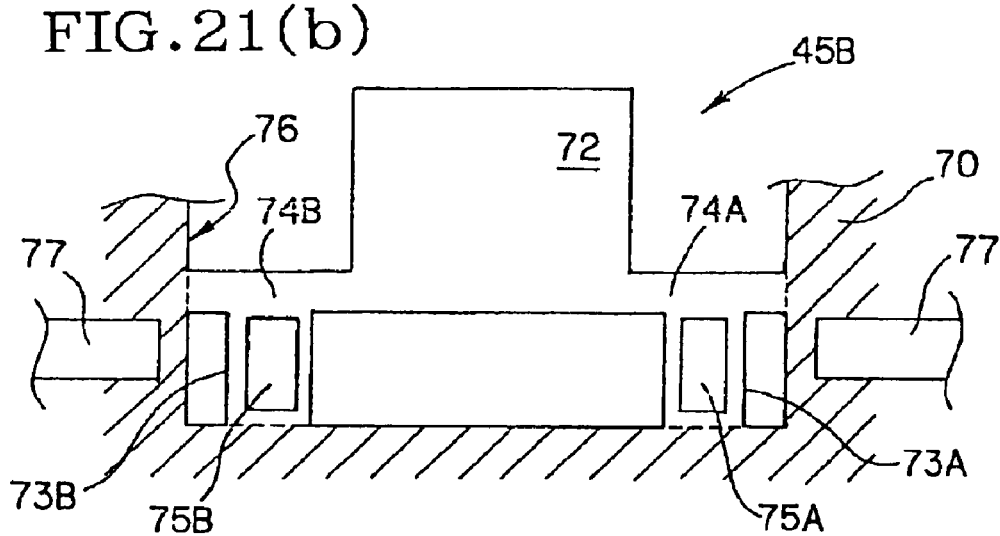
Figure 21C:
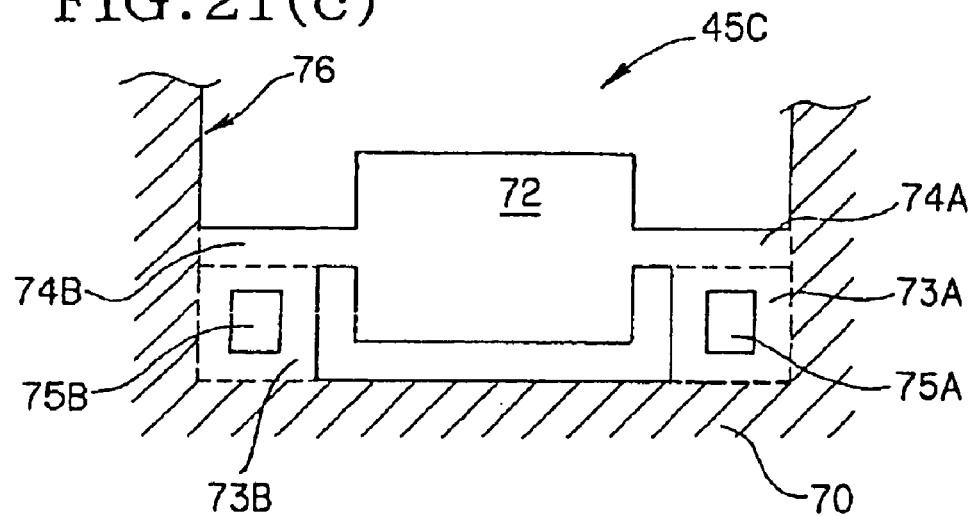

Next, FIGS. 21(a) through (c) are plans showing still another embodiment of the mass sensor of the present invention. First, in the mass sensor 45A shown in FIG. 21(a), a diaphragm 72 is joined to two connection plates 74A, 74B at respective sides so that the connection plates 74A, 74B sandwich the diaphragm 72, and the connection plates 74A, 74B bridge across the side walls of the depression 76 of the sensor substrate 70 at respective sides. Here, the depression 76 has a similar function as the cut portion 16 formed in the mass sensor 1, and therefore, may be formed on the side or other portions of the sensor substrate 70 similarly to the circumference of the sensor substrate 2 shown in FIG. 11 or the opening 14 formed in the sensor substrate 2.

The sensing plates 73A, 73B are provided across the connection plates 74A, 74B and the bottom of the depression 76 in the direction where connection plates 74A, 74B sandwich the diaphragm 72, that is, in the direction perpendicular to the Y-axis direction. Furthermore, piezoelectric elements 75A, 75B are installed on at least one of the plate surfaces of the sensing plates 73A, 73B, respectively. Thus a resonating portion is formed of the diaphragm 72, connection plates 74A, 74B, sensing plates 73A, 73B, and piezoelectric elements 75A, 75B.

The structure of the mass sensor 45A can be summarized as a mass sensor having at least one piezoelectric element, in which a diaphragm 72 is sandwiched by and joined to two connection plates at respective sides, the connection plates 74A, 74B bridge across the side walls of the opening or gap formed in the sensor substrate 70, and at least a plurality of sensing plates 73A, 73B are provided across the connection plates 74A, 74B and the sides of the opening or gap in the direction perpendicular to the direction where the respective connection plates 74A, 74B sandwich the diaphragm 72.

In such a mass sensor 45A, the resonant frequency of the resonating portion on the basis of at least some of, the θ-mode swing oscillation in which the diaphragm 72 performs pendulum-like oscillation on the fixed surface where respective connection plates 74A, 74B are joined to the sensor substrate 70, centered on the perpendicular axis where the diaphragm 72 perpendicularly passes through the fixed surface, that is the Y-axis, and in the direction perpendicular to the side of the diaphragm 72 and perpendicular to the Y-axis, that is the X-axis; the φ-mode swing oscillation in which the diaphragm 72 performs pendulum-like oscillation centered on the Y-axis in the X-axis direction accompanying the swing in the direction parallel to the side of the diaphragm 72, that is the Z-axis (not shown); swing oscillation in which the diaphragm 72 performs oscillation centered on the Y-axis in the X-axis direction; or rotational oscillation in the plate surface of the diaphragm 72; can be measured by the piezoelectric elements 75A, 75B installed on the sensing plates 73A, 73B.

The structures of mass sensors 46A through 46F described later can also be summarized similarly to the mass sensors 45A through 45C, and the method for mass sensing with the mass sensors 46A through 46F is the same as that of the mass sensors 45A through 45C. However, in the mass sensors 46A through 46F, the number of the sensing plates is increased to four, and in these embodiments, there is added the structure in which at least a plurality of sensing plates 73A through 73D bridge between the diaphragm 72 and the side of the opening or gap in the direction perpendicular to the direction where respective connection plates 74A, 74B sandwich the diaphragm 72.

Therefore, since the diaphragm 72 and the sensing plates 73A, 73B are oscillated in the direction of arrow K in FIG. 21, that is, making the Y-axis the center of oscillation, and the direction parallel to the plate surface of the diaphragm 72 and also perpendicular to the Y-axis, that is the X-axis direction, the diaphragm 72 oscillates in the direction of arrow K stably in the rigid body mode as the θ-mode of the diaphragm 72. There is also an advantage that the flexural mode of the diaphragm 72 is restricted. The shape of the diaphragm 72 is not limited to rectangular as shown in FIGS. 21(a) through (c), but optional shapes as shown in FIG. 10 can be adopted, and as in the mass sensor 45B shown in FIG. 21(b), the diaphragm 72 may be joined to respective connection plates 74A, 74B at optional locations. Furthermore, as in the mass sensor 45C shown in FIG. 21(c), the respective sensing plates 73A, 73B may be supported and fixed at three sides by the respective connection plates 74A, 74B and the sensor substrate 70 in the same way as the sensing plate 21 in the mass sensor 42 shown in FIG. 15. In the mass sensor 45B, a position sensor 77 similar to the position sensors 4,5 of the mass sensor 1 is installed.

Next, in mass sensors 46A through 46F, still other embodiments of the present invention shown in the plan of FIGS. 22(a) through (f), a diaphragm 72 is sandwiched by and joined to two connection plates 74A, 74B at respective sides, the respective connection plates 74A, 74B bridge across the side walls of the opening 71 of the sensor substrate 70, and at least a plurality of sensing plates, here sensing plates 73A through 73D, are provided between the respective connection plates 74A, 74B and the side wall of the opening 71, or between the diaphragm 72 and the side wall of the opening 71 in the direction perpendicular to the direction where the connection plates 74A, 74B sandwich the diaphragm 72.

Furthermore, piezoelectric elements 75A through 75D are installed on at least one of the plate surfaces of at least one of the sensing plates 73A through 73D, and thus a resonating portion is formed of a diaphragm 72, connection plates 74A, 74B, sensing plates 73A through 73D, and piezoelectric elements 75A through 75D.

Figure 22A:
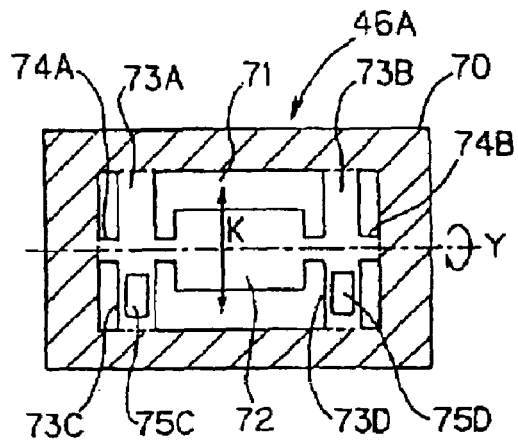
FIGS. 22(a)–(f) are diagrams showing still another embodiment of a mass sensor of the present invention; (a) through (d) and (f) are plans showing various structures in which a sensing plate is joined to connection plates; and (e) is a plan showing a structure in which a sensing plate is connected to a diaphragm.

When mass sensors 46A through 46F shown in FIGS. 22(a) through (f) are seen, in the mass sensor 46A shown in FIG. 22(a), rotation of the diaphragm 72 about the Y-axis is restricted by the sensing plates 73A, 73B compared with the structures of mass sensors 45A through 45C shown in FIG. 21. It is preferable to form slits 28 on the sensing plates 73A, 73B as in the embodiment shown in FIG. 17 because the diaphragm 72 oscillates easily in the direction of arrow K.

Figure 22B:
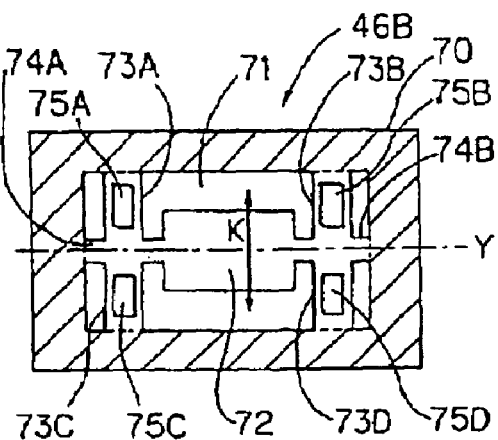

In the mass sensor 46B of FIG. 22(b), piezoelectric elements 75A through 75D are installed on the surfaces of all of the sensing plates 73A through 73D shown in FIG. 22(a) oriented to the same direction. By this, the amplitude of the diaphragm 72 oscillating in the K direction is increased, and the mass sensor can be suitably used for the measurement in high viscous substances as well as in low viscous substances. At this time, the direction of the polarization of piezoelectric films of the piezoelectric elements 75A and 75C, and 75B and 75D should be opposite to each other. Furthermore, the piezoelectric elements 75A through 75D may be installed on both sides of the sensing plates 73A through 73D.

Figure 22C:
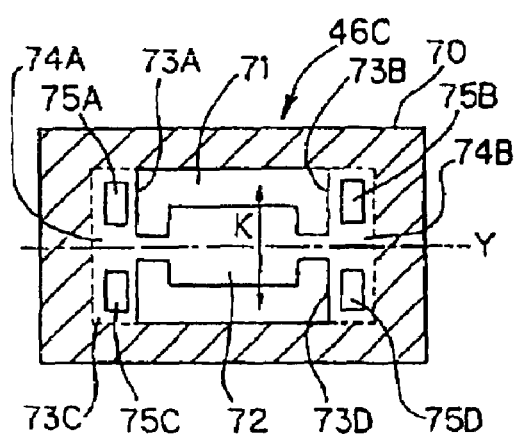

FIG. 22(c) shows a mass sensor 46C in which a side of sensing plates 73A through 73D in the embodiments shown in FIGS. 22(a) and (b) facing to the sensor substrate 70 is joined to the sensor substrate 70. By such a structure, the effects obtained by the structure of the mass sensor 42 shown in FIG. 15 can be added to the effects of the embodiments shown in FIGS. 22(a) and (b).

Figure 22D:
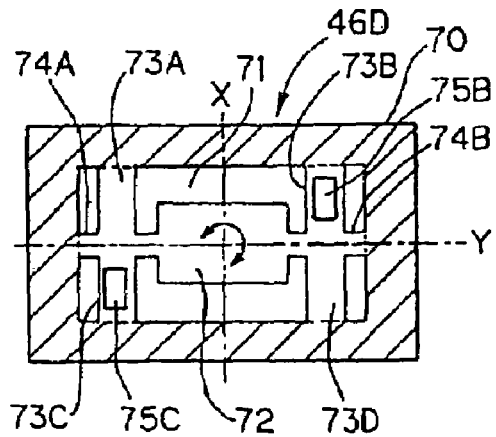

In the mass sensor 46D of FIG. 22(d), piezoelectric elements 75B, 75C are installed on the sensing plates 73B, 73C located point-symmetrically about the intersection of the X-axis and the Y-axis, which is the center of the diaphragm 72. Since the resonant frequency is sensed using the rigid body mode in which oscillation in the η direction around the intersection of the X-axis and the Y-axis (direction of the arrow in FIG. 22(d)) is dominant, the sensing plates 73A, 73D are not necessarily required. When the sensing plates 73A, 73D are formed, slits or piezoelectric elements 75A, 75D may be provided on the sensing plates 73A, 73D. In this case, it is preferable that the directions of polarization of respective piezoelectric films in each set of the piezoelectric elements 75A and 75D, and 75B and 75C are the same.

Figure 22E:
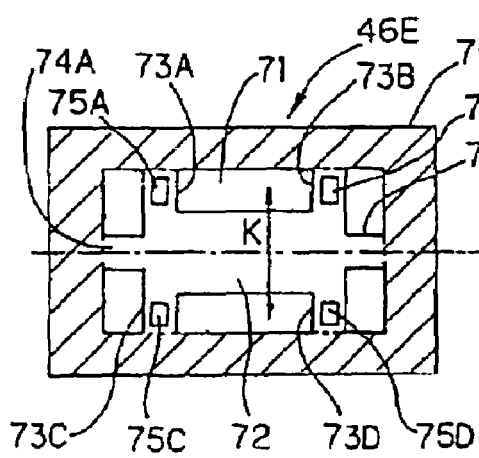
Figure 22F:
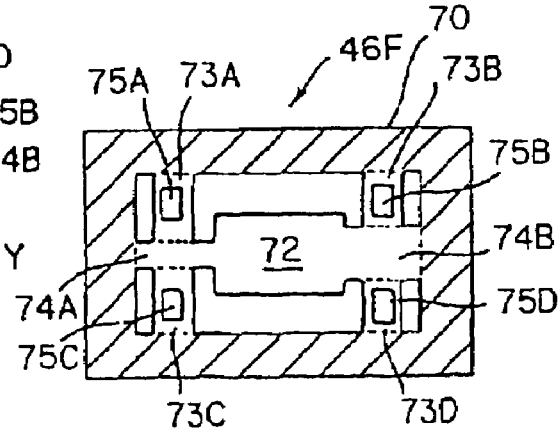

In the mass sensor 46E of FIG. 22(e), sensing plates 73A through 73D are joined to the diaphragm 72, and the locations of the piezoelectric elements 75A through 75D are the same as in the case of FIG. 22(b). The oscillation of the diaphragm 72 in the direction of arrow K can also be sensed by such a structure. Furthermore, the mass sensor 46F shown in FIG. 22(f) has the structure which oscillates easily in the θ-mode and the φ-mode by increasing the width of either one of the connection plates 74A, 74B, and decreasing the width of the other.

Thus, although various shapes can be selected in the mass sensors of the present invention, materials used for producing these mass sensors are not changed depending on respective mass sensors. Then, members constituting a mass sensor of the present invention and their shapes will be described using the mass sensor 1 described above. First, the sensor substrate 2, diaphragm 19, connection plate 20, sensing plate 21, and spring plate 18 are preferably made of ceramics, for example, stabilized or partially stabilized zirconia, alumina, magnesia, or silicon nitride. Among these, stabilized or partially stabilized zirconia is most preferably used because they have a high mechanical strength even in case of a thin plate, a high toughness, and a low reactivity with the materials of piezoelectric films or electrodes.

When stabilized or partially stabilized zirconia mentioned above is used as the material for the sensor substrate 2, it is preferable to add an additive such as alumina and titania at least to the sensing plate.

Although the oscillation plate 3, intermediate plate 17, and base plate 15 in the sensor substrate 2, and the diaphragm 19, connection plate 20, spring plate 18, and sensing plate 21 are not necessarily required to be composed of the same material, and various ceramic materials may be used in combination depending on the design, it is preferable to constitute these members integrally using the same material from the point of view of the reliability of the parts where these members are joined, and the simplification of the manufacturing process.

However, when the spring plates 18 are formed on both the plate surfaces of a connection plate 20, the spring plate formed on the surface on which a piezoelectric element 25 is installed can be produced to have the same structure as the piezoelectric element 25. This is preferable for the manufacturing process, since the spring plate can be formed simultaneously with the piezoelectric element 25. However, for the piezoelectric element formed as a spring plate, the electrode is not used as the electrode.

Although a major purpose of the mass sensor 1 is sensing a mass of the 0.1 nanogram (ng) order, the thickness of the diaphragm 19 is preferably about 3 to 20 μm, more preferably about 5 to 15 μm, and the thickness of the base plate 15 is suitably determined considering the ease of operation.

When a spring plate 18 is formed, in either case where it is bonded on one side or on both sides of the connection plate 20, the thickness is preferably 10 to 220 μm, the width is preferably 100 to 500 μm, and the aspect ratio (width/thickness) of the spring plate 18 is preferably in a range between 0.4 and 50. When the attenuation of oscillation amplitude by the use of the mass sensor 1 in a liquid is considered, the thickness is preferably 10 to 70 μm, the width is preferably 100 to 500 μm, and the aspect ratio is preferably 1.4 to 50. More preferably, the thickness is 10 to 70 μm, the width is 100 to 300 μm, and the aspect ratio is 1.4 to 30. The thickness of the spring plate reinforcement, when such a spring plate reinforcement is required, is preferably the same as the thickness of the spring plate being joined to the spring plate reinforcement.

Whereas, the connection plate 20 may be used as a spring plate without forming the spring plate 18. In this case, no intermediate plate 17 may be formed, but it is preferable to increase the thickness of the base plate 15 by the thickness of the intermediate plate 17 for maintaining the mechanical strength of the sensor substrate 2.

For the piezoelectric film 23 in the piezoelectric element 25, although film-like piezoelectric ceramics are suitably used, electrostriction ceramics or ferroelectric ceramics may also be used. Such materials may be either those requiring or not requiring polarization.

Ceramics that can be used in the piezoelectric film 23 include, for example, lead zirconate, lead titanate, lead magnesium niobate, lead nickel niobate, lead zinc niobate, lead manganese niobate, lead antimony stannate, lead manganese tungstate, lead cobalt niobate, and barium titanate. These may be used alone, or as ceramics containing the combination of some of them. In the present invention, a material containing the components consisting mainly of lead zirconate, lead titanate, and lead magnesium niobate as the main component is preferably used, because such a material not only has high electrical-mechanical coupling coefficient and piezoelectric constant, but also has small reactivity with the sensor substrate member on sintering piezoelectric film, and can form the desired composition stably.

Furthermore, ceramics containing the oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth, and tin alone, or in the combination of some of these oxides, or ceramics in which other compounds of these elements are added may be used for the above piezoelectric ceramics. For example, a ceramic material containing lead zirconate, lead titanate, and lead magnesium niobate as main components, to which lanthanum or strontium is added is also preferable, and such a material to which manganese is further added is preferable because the mechanical quality factor is large, and the Q value can be increased not only from the structure of the sensor but also from the material.

On the other hand, the first electrode 22 and the second electrode 24 in the piezoelectric element 25 are preferably formed from a metal that is solid at room temperature and conductive. For example, a metal such as aluminum, titanium, chromium, iron, cobalt, nickel, copper, zinc, niobium, molybdenum, ruthenium, palladium, rhodium, silver, tin, tantalum, tungsten, iridium, platinum, gold, or lead alone, or an alloy of some of these elements can be used. Furthermore, a cermet material in which the same material used in the piezoelectric film 23 or the sensing plate 21 is dispersed in these materials may be used.

The selection of the material for the actual first electrode 22 and the second electrode 24 is determined depending on the method for forming the piezoelectric film 23. For example, when the first electrode 22 is formed on the sensing plate 21, then the piezoelectric film 23 is formed on the first electrode 22 by sintering, the first electrode 22 must be made of a high melting point metal, such as platinum, which is not affected by the temperature for sintering the piezoelectric film 23. However, since the second electrode formed on the piezoelectric film 23 after forming the piezoelectric film 23 can be formed at a low temperature, a low melting point metal, such as aluminum, can be used.

Although the piezoelectric element 25 can be formed integrally by sintering, in this case, both the first electrode 22 and the second electrode 24 must be made of a high melting point metal which resists the temperature for sintering the piezoelectric film 23. On the other hand, when the first and second electrodes 59, 60 are formed on the piezoelectric film 58 after forming the piezoelectric film 58, as in the piezoelectric element 62A shown in FIG. 3, both electrodes can be made of the same low melting point metal, but when the piezoelectric element 62A is simultaneously sintered, both the first electrode 22 and the second electrode 24 must be made of a high melting point metal. Thus, the materials for the first electrode 22 and the second electrode 24 can be selected suitably depending on the temperature for forming the piezoelectric film 23 represented by the sintering temperature of the piezoelectric film 23, and the structure of the piezoelectric element 25. The materials and methods for forming the electrode leads 9, 10 are the same as those for the first electrode 22 and the second electrode 24 of the piezoelectric element 25.

Since a problem arises when the area of the piezoelectric film 23 is expanded, in that although sensitivity increases because of increase in the output charge, the size of the sensor increases, the area of the piezoelectric film 23 should be designed to an adequate size. Also, since a problem arises when the thickness of the piezoelectric film 23 is decreased, in that although sensitivity increases, the rigidity of the piezoelectric film 23 is lowered, the total thickness of the sensing plate 21 and the piezoelectric film 23 is preferably 15 to 50 µm.

When an insulation coating layer 65 is formed on the piezoelectric element 25 and the electrode leads 9, 10 as in the mass sensor 43D shown in FIG. 19, insulating glass or resin is used as its material. For enhancing the performance of the mass sensor 1, a resin is more preferably used as the material for the insulation coating layer than glass, and chemically stable fluorine resins, for example, tetrafluoroethylene-based Teflon (Teflon PTFE of DuPont), tetrafluoroethylene-hexafluoropropylene copolymer-based Teflon (Teflon FEP), tetrafluoroethylene-perfluoroalkyl vinyl ether copolymer-based Teflon (Teflon PFA), and PTFE/PFA composite Teflon are preferably used. Although corrosion resistance and weather resistance are lower than those of these fluorine resins, silicone resins (in particular, thermosetting silicone resins) can be suitably used, and epoxy resins or acrylate resins can also be used depending on the applications. It is also preferable to form the insulation coating layer 65 using different materials for the piezoelectric element 25 and its vicinity, and the electrode leads 9, 10 and their vicinity. Furthermore, it is also preferable to add inorganic or organic fillers in the insulating resin to adjust the rigidity of the resonating portion.

When the insulation coating layer 65 is formed, the materials for a shield layer 66 formed on the insulation coating layer 65 are preferably metals such as gold, silver, copper, nickel, and aluminum; however, any metallic materials used in the first electrode 22 of the piezoelectric element 25 or the like described above can be used. A conductive paste comprising metal powder mixed in a resin may also be used.

Next, the method for using a mass sensor of the present invention will be described when the mass sensor 1 is used as an immune sensor. One of two sensor portions 13 is used as a detection sensor portion 13D. To the diaphragm of the detection sensor portion 13D is applied a catching substance which reacts with only a substance to be sensed, such as a pathogenic virus, and catches it. For example, the combination of an antigen as the substance to be sensed, and an antibody as the catching substance can be used. The examples of such combinations include human serum albumin/anti-human serum albumin antibody and human immunoglobulin/anti-human immunoglobulin antibody. Whereas, the other sensor portion 13 is used as a reference sensor portion 13R, to the diaphragm of which no catching substance is applied.

Both sensor portions 13D and 13R are immersed in or placed on the same specimen. In many cases, since specimens are fluids such as liquids or gases, the specimens can be tested by comparing the signals from the sensor portions 13D and 13R, without being influenced by the physical properties of the specimens such as type and, flow, and temperature of the fluid, or the testing environment.

When this mass sensor 1 is immersed in, for example, a conductive liquid specimen, if the mass sensor 1 is immersed in the specimen to the level where the position sensor electrodes 4, 5 are short-circuited, the diaphragms 19 of the sensor portions 13D and 13R are immersed in the specimen, but the sensing portion 29 is not short-circuited by the specimen. However, when the piezoelectric element 25 and the electrode leads 9, 10 are coated by insulating glass or resin, the areas of the mass sensor 1 other than terminals 11, 12, or other connectors, can be immersed in the specimen.

Thus, when the substance to be sensed in the specimen reacts with and is caught by the catching substance, the mass of the diaphragm 19 in the detection sensor portion 13D increases, and the resonant frequency of the resonating portion 26 varies accompanying this increase in the mass of the diaphragm 19. Therefore, on the contrary, by observing change in the resonant frequency of the resonating portion 26, whether or not the substance to be sensed has been caught on the diaphragm 19, that is, whether or not the substance to be sensed was present in the specimen, can be determined, and increase in the mass can be measured.

In the method for using the two sensor portions 13 as a detection sensor portion 13D and a reference sensor portion 13R, if the resonating portion in the reference sensor portion 13R, that is, the diaphragm, connection plate, sensing plate, piezoelectric element, and spring plate are coated by Teflon, the adhesion of the substance to be sensed to the reference sensor portion 13R can be prevented, and more accurate measurement can be performed. If the detection sensor portion 13D other than the diaphragm 19 is similarly coated by Teflon, the substance to be sensed can be caught only on the diaphragm 19, and sensitivity is elevated. Furthermore, it is economically preferable to coat the entire sensor substrate 2 other than the diaphragm 19 with Teflon in order to apply an expensive catching substance such as an antibody only to a required location.

When the mass sensor 1 is immersed in a specimen, such as a liquid, or a diaphragm 19 is dipped in a catching substance for applying the catching substance to the diaphragm 19, the structure is adopted in which two sensor portions 13 are arranged in the lateral direction of the sensor substrate 2 (horizontal direction) in FIG. 11, so that the two sensor portions 13 are simultaneously immersed in the specimen.

However, if the two sensor portions 13 are arranged in the perpendicular direction of the sensor substrate 2 (up-down direction), that is, on the position where the detection sensor portion 13D is first immersed in the liquid, and the reference sensor portion 13R is not immersed in the liquid, the process can easily be performed, in which only the area of the detection sensor portion 13D is immersed in the catching substance for applying, and the reference sensor portion 13R is used as a sensor such as a temperature compensating sensor without teflon coating, and is not immersed in the catching substance, that is not to apply the catching substance.

However, even in using the mass sensor 1 in which the catching substance is applied only to the detection sensor portion 13D, the detection sensor portion 13D and the reference sensor portion 13R must be placed in the same environment on actual mass sensing. Also, when the entire mass sensor 1 is immersed in a conductive liquid, the piezoelectric elements 25 and the electrode leads 9, 10 in the sensor portions 13R, 13D must obviously undergo insulation coating.

The using method, in which the same catching substance is applied to the diaphragms of both sensor portions 13D and 13R to expand the dynamic range by adding the signals from the sensor portions 13D and 13R, is also possible. Furthermore, it is also possible not to use the reference sensor portion 13R for referencing, and a catching substance different from that applied to the detection sensor portion 13D is applied to the reference sensor portion 13R.

On the measurement of change in the resonant frequency in the mass sensor 1 with these using methods, it is preferable to sense the resonant frequencies in the θ-mode and the φ-mode as described above. For example, as FIG. 14 shows, when the diaphragm 19 generates swing oscillation in the θ-mode about the spring plate 18 and the connection plate 20 in the plate surface of the diaphragm 19, the movement is transmitted to the sensing plate 21 to cause the bending oscillation of the sensing plate 21 and the stretching oscillation of the planer piezoelectric film 23 in the piezoelectric element 25 on the surface of the sensing plate 21, and a constant voltage is generated on the basis of the electrical-mechanical coupling coefficient $k_{31}$ (piezoelectric factor $d_{31}$) of the piezoelectric film 23. When the piezoelectric element 25 has a comb-shaped electrode structure, a constant voltage is generated on the basis of $k_{33}$ ($d_{33}$). This is the same when the φ-mode is used.

On the contrary, when an alternating current is applied to the piezoelectric film 23 through the second electrode 24 and the first electrode 22, stretching oscillation is generated in the piezoelectric film 23 by $d_{31}$ or $d_{33}$ causing the sensing plate 21 to generate bending oscillation, and the oscillating angle θ of the diaphragm 19 varies corresponding to the mass of the diaphragm 19, and resonant oscillation is generated at a certain frequency. Therefore, the observation of change in the resonant frequency is the observation of change in the mass of the diaphragm 19, and whether or not a substance to be sensed is caught on the diaphragm 19 can be determined. By installing two piezoelectric elements 25 on both plate surfaces of the sensing plate 21 and comparing obtained signals, noise can be reduced, the effect of other oscillation modes can be eliminated, and sensitivity can be improved.

Here, in order to further improve the sensitivity of the mass sensor 1, change in the resonant frequency of the resonating portion 26 must be increased. As a means for this, a method for controlling the ratio of masses of the diaphragm 19 and the spring plate 18 can be used. As the spring plate 18 is thinned to reduce the mass, and the mass ratio with the diaphragm 19 (mass of the diaphragm 19/mass of the spring plate 18) is increased, sensitivity is improved.

However, since the rigidity of the spring plate 18 is lowered with decrease in the thickness and the mass of the spring plate 18, the mass ratio (mass of the diaphragm 19/(mass of the spring plate 18+mass of the connection plate 20)) is preferably 0.1 or more within a range where the rigidity of the spring plate 18 and the connection plate 20 is secured, considering the thickness and area of the diaphragm 19, but it is preferable to determine the suitable ratio considering the area of the diaphragm 19. However, these mass ratios are preferably determined within the range where the conditions of the thickness, width, and the aspect ratio of the spring plate 18 described above are satisfied. The mass sensor 43C shown in FIG. 16(c) is one of the examples.

As another means for improving sensitivity, a method to decrease the thickness of the diaphragm 19 for increasing the mass ratio with a substance to be sensed (mass of the substance to be sensed/mass of the diaphragm 19), that is, the proportion of change in the mass of the diaphragm 19 can be used. Furthermore, when the thickness of the diaphragm 19 is decreased, if the surface area of the diaphragm 19 is increased without decreasing the mass, the area to which the catching substance is applied can be increased, and more substance to be sensed can be caught, resulting in the improvement of sensitivity.

Next, other applications of the mass sensor 1 will be described. First, when the catching substance applied to the diaphragm 19 is a moisture adsorbing material, the mass sensor 1 can be used as a moisture meter. When applying to the diaphragm 19 an adsorbing material that adsorbs a specific gaseous component, or an organic or inorganic substance as a catching substance, the mass sensor 1 can be used as a gas sensor, an odor sensor, or a taste sensor. Furthermore, if the temperature of the diaphragm 19 is controlled to make moisture condense, the mass sensor 1 can be used as a dew point meter which measures the dew point from the temperature when the mass of the diaphragm 19 is increased.

The mass sensor 1 can also be used as a film thickness meter. The films that can be measured include sputtered films or CVD films formed in vacuum, LB films formed in gases, or electrodeposited films formed in liquids. When these films are formed, if the diaphragm 19 or the resonating portion 26 of the mass sensor 1 is placed in the same film forming environment, a film is formed on the diaphragm 19 or the resonating portion 26 causing change in the mass, and change in resonant frequency, the thickness or the growing speed of the formed film can be measured.

Figure 27:
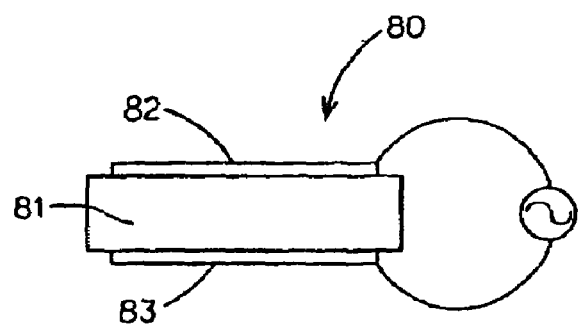
FIG. 27 is a sectional view illustrating the basic structure of a conventional micro-mass sensor.

Although a quartz vapor deposited film thickness meter has been known to detect change in the resonant frequency of a quartz oscillator 80 similar to the one shown in FIG. 27 in the slipping direction when the film thickness changes, it has problems in that it is affected by change in temperature, noise due to the collision of impurities, and change in vacuum pressure, because the oscillator itself is used in a vapor deposition environment.

Whereas, if the mass sensor 1 is used in the θ-mode as a vapor deposited film thickness meter, the sensing portion 29 resists change in temperature because of the rigid body mode, the probability of the collision of impurities is low because the diaphragm 19 is as thin as 3 to 20 μm, and a structure in which the sensing portion 29, spring plate 18, and the connection plate 20 are easily held in a constant environment, the measurement accuracy can be improved compared with the case where a quartz oscillator 80 is used.

Furthermore, the mass sensor 1 can be used as a viscosity meter to cause the shear waves of transverse waves to occur in a fluid when the diaphragm 19 is immersed in the liquid, and receive the mass load of the portion where viscous waves enter.

Although a quartz viscosity meter for detecting change in the resonant frequency of a quartz oscillator 80 in the slipping direction is also used, it has problems in that it is affected by change in temperature, and noise due to the collision of impurities in the liquid, because the quartz oscillator 80 itself is immersed in the liquid.

On the other hand, when the mass sensor 1 is used in the θ-mode as a viscosity meter, since the sensing portion 29, the spring plate 18, and the connection plate 20 are not required to be immersed in the liquid, the sensing portion 29 resists change in temperature because of the rigid body mode, and the diaphragm 19 is as thin as 3 to 20 μm, the probability of the collision of impurities is low, sensitivity is improved.

Furthermore, a quartz oscillator is used as a friction vacuum meter since its electric resistance varies due to the friction of gas molecules and the viscous friction of the gas in a vacuum. However, since this type of vacuum meter is used to measure change in frequencies due to the mass load effect of the quartz oscillator, the mass sensor 1 of the present invention utilizing basically the same measurement principle can also be used as a vacuum meter.

Figure 28:
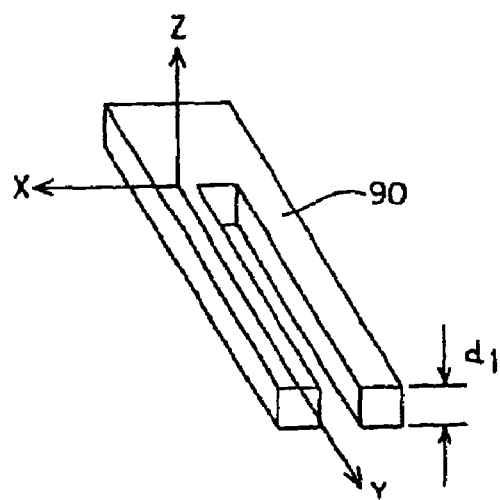
FIG. 28 is a perspective view showing the structure of a quartz oscillator of a conventional quartz friction vacuum meter.

Although a friction vacuum meter using a quartz oscillator detects change in resistance when the tuning fork-shaped oscillator 90 is oscillated in the X-axis direction as FIG. 28 shows, it is difficult to decrease the thickness d, of the oscillator 90, and therefore, the improvement of sensitivity is difficult. Whereas, in the mass sensor 1, the thickness of the diaphragm 19 can be decreased to 3 to 20 μm, and the θ-mode can be used, sensitivity can be improved.

In addition, the mass sensor 1 can be used as a temperature sensor by using the bending mode of the diaphragm 19, that is, by sensing change in the Young's modulus as change in resonant frequency in the bending mode.

Although the mass sensor 1 can be used as various sensors, the basic principle of measurement is to measure change in the resonant frequency of the resonating portion 26 on the basis of the mass load to the diaphragm 19. Therefore, a plurality of sensor portions 13 having different functions can be formed easily in one mass sensor 1. For example, the functions of a temperature sensor, a vacuum meter, or a viscosity sensor can be added to the function as the mass sensor 1, that is, a sensor for referencing for the compensation of temperature, vacuum, or viscosity can be easily incorporated in the mass sensor 1. In such cases, since it is not necessary to use a plurality of sensors having different shapes for different applications, it is also advantageous from the costs for the incorporation of sensors to the place of measurement and their handling, and for the measuring instruments.

Next, a method for fabricating a mass sensor of the present invention will be described using the mass sensor 1 as an example. As the materials of the sensor substrate, ceramics such as zirconia are suitably used. A slurry is produced by mixing a binder, solvent, dispersing agent, and other additives in ceramic powder, and after removing foams from the slurry, a green sheet or a green tape for the oscillation plate, intermediate plates and base plates having desired thickness using a method such as the reverse roll coater method and the doctor blade method is formed.

Figure 23:
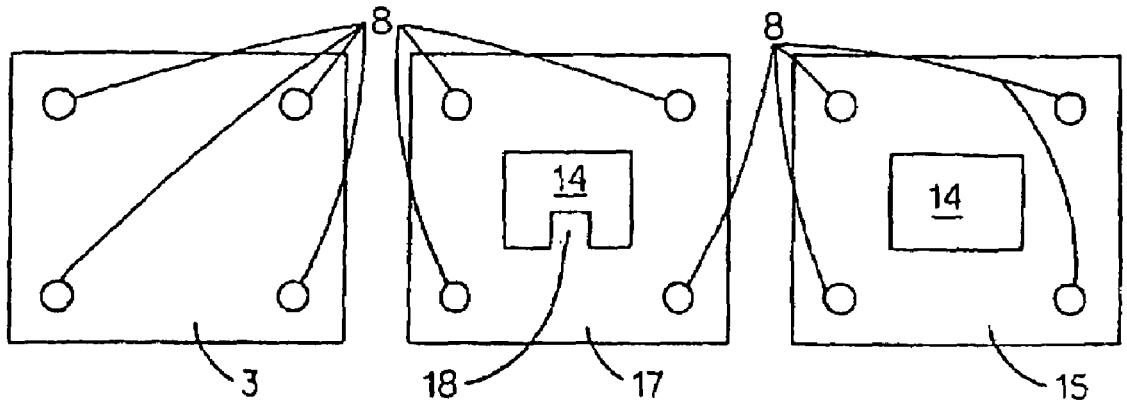
FIG. 23 is a plan showing an example of processing a green sheet for a sensor substrate used in the fabrication of a mass sensor of the present invention.

Next, these green sheets are punched using a die or laser to desired shapes, for example, as shown in FIG. 23, the shape of an intermediate plate 17 having an opening 14 and a spring plate 18, and the shape of a base plate 15 having an opening 14, and the green sheet at least one for each of the oscillation plate, the intermediate plate 17, and the base plate 15 are laminated in this order, and sintered and integrated to form the sensor substrate. On laminating these green sheets, holes 8 are formed in each green sheet for the alignment of lamination. The shapes of the green sheets shown in FIG. 23 are simplified for easy understanding of the formation of the sensor portion 13 of the mass sensor 1 shown in FIG. 11.

Although an opening 14 or a diaphragm 19 can be also formed in the oscillation plate 3 in green state, since the oscillation plate is as thin as 20 μm or lesser, it is preferable to form the opening 14 or the diaphragm 19 in a predetermined shape after forming the sensor substrate 2 and installing the piezoelectric element 25 by laser processing described later, for securing the flatness and dimensional accuracy after sintering of the diaphragm 19, connection plate 20, and sensing plate 21 formed in the oscillation plate 3.

Methods for installing the piezoelectric element 25 consisting of a first electrode 22, a piezoelectric film 23, and a second electrode 24 on the area of the oscillation plate 3 where the sensing plate 21 is formed include a method in which a piezoelectric film 23 is formed by press formation using a die or tape formation using a slurry material, the piezoelectric film 23 before sintering is overlaid by heat and pressure on the area of the oscillation plate 3 where the sensing plate 21 is formed, and they are simultaneously sintered to form the sensor substrate 2 and the piezoelectric film 23 at the same time. In this case, however, the electrodes 22, 24 must be formed on the sensor substrate 2 or the piezoelectric film 23 beforehand by the film formation method described later.

Although the temperature for sintering the piezoelectric film 23 is determined depending on the constituting material, it is generally 800° C. to 1400° C., preferably 1000° C. to 1400° C. In this case, it is preferable for controlling the composition of the piezoelectric film 23, that sintering is conducted in the presence of the evaporation source of the material for the piezoelectric film 23. When the sintering of the piezoelectric film 23 and the sintering of the sensor substrate 2 are performed simultaneously, the sintering conditions of the two must be matched to each other.

On the other hand, if the film formation method is used, the piezoelectric element 25 can be installed on the area of the sintered sensor substrate 2 where the sensing plate 21 is formed, by various thick film forming methods, such as screen printing, dipping, and painting; or various thin film forming methods, such as the ion beam method, sputtering, vacuum deposition, ion plating, chemical vapor deposition (CVD), or electroplating. Among these, for the formation of the piezoelectric film 23 in the present invention, thick film forming methods, such as screen printing, dipping, and painting are preferably used. This is because the piezoelectric film 23 can be formed using paste or slurry consisting mainly of the particles of piezoelectric ceramics having an average particle diameter of 0.01 to 5 µm, preferably 0.05 to 3 µm, and favorable piezoelectric properties are obtained.

For example, after the sensor substrate 2 has been sintered under predetermined conditions, the first electrode 22 is printed and sintered on the predetermined surface area of the oscillation plate 3, then the piezoelectric film 23 is printed and sintered, and further, the second electrode 24 is printed and sintered to form the piezoelectric element 25. Then, electrode leads 9, 10 are printed and sintered for connecting the electrodes 22, 24 to the measurement apparatus. Here, for example, if platinum (Pt) is used for the first electrode 22, lead zirconate titanate (PZT) is used for the piezoelectric film 23, gold (Au) is used for the second electrode 24, and silver (Ag) is used for the electrode leads 9, 10, sintering temperatures in the sintering process can be lowered stepwise. Therefore, the previously sintered materials are not sintered again in a certain sintering step, and the occurrence of troubles in the material for electrodes or the like, such as peeling off and aggregation, can be avoided.

By selecting suitable materials, the respective members of the piezoelectric element 25 and electrodes 9, 10 can be printed one after the other, and integrally sintered at once, or after the piezoelectric film 23 is formed, respective electrodes or the like can be formed at a low temperature. Also, the respective members of the piezoelectric element 25 and electrodes 9, 10 can be formed by a thin film forming method, such as sputtering or vapor deposition. In this case, heat treatment is not necessarily required.

Thus, it is particularly preferable to form the piezoelectric element 25 using the film formation method, since the piezoelectric element 25 and the sensing plate 21 can be integrally joined and installed without using adhesives, and the mass sensor excels in reliability and reproducibility, and is easily integrated. Here, the piezoelectric film 23 may be suitably patterned, and the methods for patterning include, for example, screen printing, photolithography, laser processing, or mechanical processing such as slicing and ultrasonic processing.

Next, a diaphragm 19 is formed on the predetermined area of thus formed sensor substrate. Here, it is preferable to remove the unnecessary part of the oscillation plate 3 by processing using the fourth harmonic of YAG laser. Thus, for example, an opening 14 can be formed leaving members integrally joined to the sensor substrate 2, such as the diaphragm 19 and the sensing plate 21 as shown in FIG. 11 or 12, and at this time, by adjusting the shape of the diaphragm 19 or the like, the resonant frequency can be adjusted to the predetermined value, and the range of masses of the substance to be sensed can be determined.

Figure 24:
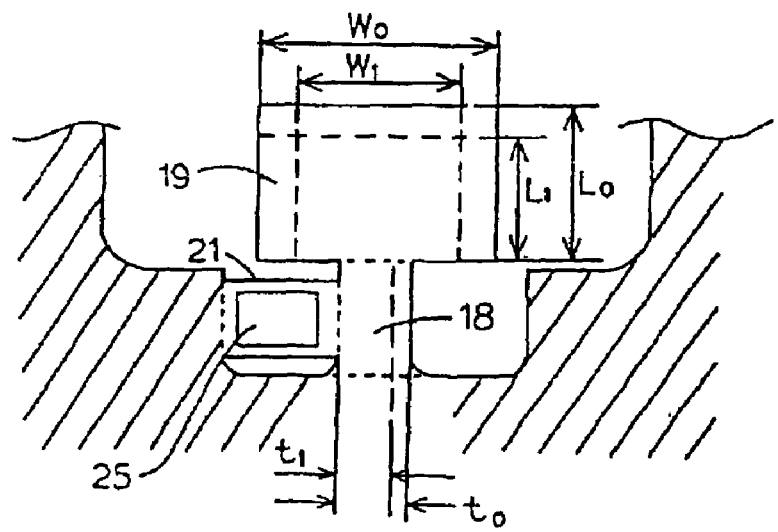
FIG. 24 is a diagram illustrating the size and shape which is preferably adjusted on the fabrication of a mass sensor of the present invention.

Here, as shown in FIG. 24 if a part of the diaphragm 19 is cut and removed so that the length of the diaphragm 19 is decreased from $L_0$ to $L_1$, the resonance point can be raised, and on the other hand, if the width of the spring plate 18 and the connection plate 20 is narrowed from $t_0$ to $t_1$, the resonance point can be lowered. Therefore, by the combination of these values, the resonance point can be adjusted. Furthermore, by narrowing the width of the diaphragm 19 from $W_0$ to $W_1$, the rotation mode can be restricted, the Q value in the θ-mode can be increased, and the difference of change in the resonant frequencies depending on an adhesion location can be decreased even when the mass of the adhered substance is the same.

Figure 25:
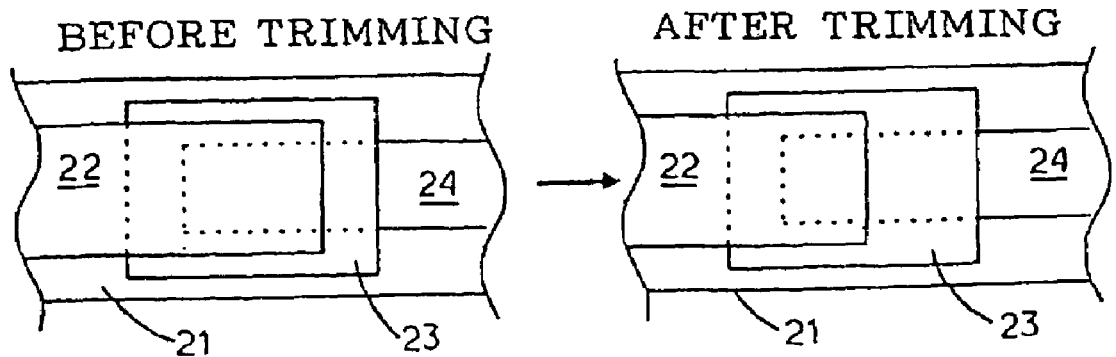
FIG. 25 is a diagram illustrating an example of processing a piezoelectric element of a mass sensor of the present invention.

Furthermore, as FIG. 25 shows, after a piezoelectric element 25 comprising a first electrode 22 as the upper electrode, a second electrode 24 as the lower electrode, and a piezoelectric film 23 formed therebetween is once formed, the upper electrode can be removed by the fourth harmonic of YAG laser, or machining to adjust the effective electrode area of the piezoelectric element and adjust sensitivity. When the structure of the piezoelectric element 25 is a comb structure as shown in FIG. 3 or 4, part of one or both electrodes may be removed.

In processing such a resonating portion, various processing methods suitable for the size and shape of the resonating portion, such as laser processing with YAG laser, the second or third harmonic of YAG laser, excimer laser, or $CO_2$ laser; electron beam processing; and dicing (machining), in addition to the fourth harmonic of YAG laser described above.

In addition to the method using green sheets as described above, the sensor substrate 2 can be produced by the compression molding using molds, slip casting, or injection molding. In these cases also, machining such as cutting, grinding, laser processing, press punching, and ultrasonic processing is conducted before and after sintering, and the mass sensor 1 of a predetermined shape is obtained.

When an insulation coating layer 65 is formed on the piezoelectric element 25 and electrode leads 9, 10 in thus fabricated mass sensor 1, as in the mass sensor 43D shown in FIG. 19, it can be formed using glass or a resin by screen printing, painting, or spraying. Here, when glass is used as the material, the mass sensor 1 itself must be heated to the softening point of the glass, and since glass has a high hardness, oscillation may be inhibited. However, since the resin is soft, and only such processing as drying is required, the use of a resin is preferable. Although it has already been described that fluorine or silicone resins are suitable as resins that can be used in the insulation coating layer 65, it is preferable, when these resins are used, to form a primer layer suited to the types of the resin and ceramics used, for improving the adhesion with the underlying ceramics, and to form the insulation coating layer 65 on the primer layer.

Next, when a shield layer 66 formed on the insulation coating layer 65 is made of a resin, since sintering is difficult, a method not requiring heat, such as sputtering, is used when various metallic materials are used as conductive members; however, when a conductive paste comprising metal powder and a resin is used, screen printing or painting can be used preferably. If the insulation coating layer 65 is made of glass, a paste containing a metal can be screen-printed, and sintered below a temperature at which the glass flows.

Finally, a catching substance or the like is applied to the entire diaphragm 19 or resonating portion 26 to complete the mass sensor 1. The measurement of resonant frequencies is performed using an impedance analyzer or a network analyzer, or by the SINSWEEP system, or through the measurement of transfer functions by oscillating by external ultrasonic waves. Furthermore, change in the mass of the diaphragm 19 can be measured from change in the resonant frequencies.

The present invention will be described below referring to the example; however, this example is not intended to limit the present invention.

In the fabrication of the mass sensor having the structure shown in FIG. 11, green sheets having different thicknesses were prepared for the oscillation plate, the intermediate plate, and the base plate from zirconia which had been partially stabilized by yttrium oxide, processed in predetermined shapes, laminated in this order, heated and compressed, and integrally sintered at 1450° C. Next, a piezoelectric element consisting of a first electrode, a piezoelectric film, and a second electrode, and electrode leads connected to these electrodes were formed on the predetermined area of the oscillation plate on which the sensing plate was formed by the screen-print method. The first electrode was made of platinum; the piezoelectric film was made of a material containing lead zirconate, lead titanate, and lead magnesium niobate as main components; the second electrode was made of gold; and the electrode leads were made of silver.

Next, YAG laser processing (fourth harmonic, wavelength: 266 nm) was performed so that an opening, a diaphragm, and a sensing plate were formed in the sensor portion 13 shown in FIG. 12 to complete the mass sensor 1. Here, the thickness of the diaphragm was 7 μm, the thickness of the intermediate plate was 65 μm, the thickness of the base plate was 150 μm, and the dimension of the diaphragm was 0.5 mm×0.3 mm.

Figure 26:
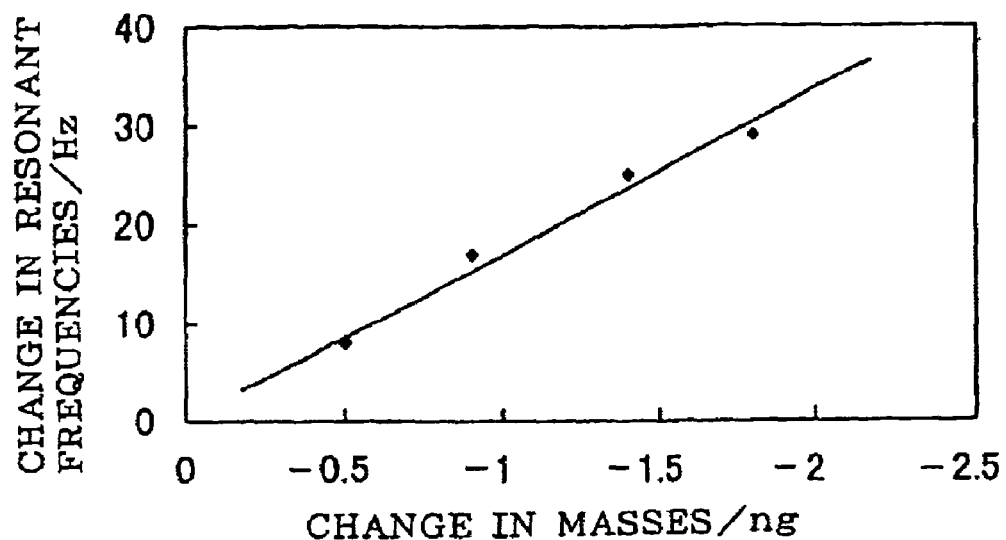
FIG. 26 is a diagram illustrating operation properties of a mass sensor of the present invention.

The mass on the diaphragm was changed by forming a plurality of spot patterns of 10 μmφ in diameter in a gold layer of a thickness of 0.3 μm formed on an entire surface of the diaphragm with YAG laser as described above to decrease the mass. The resonant frequencies before and after processing were observed, and the results shown in FIG. 26 were obtained. From these results, it was verified that the mass sensor of the present invention exhibited change in resonant frequencies corresponding to change in the mass of a nanometer order.

The mass sensor of the present invention has been described focussing a piezoelectric conversion device using a piezoelectric film that utilizes the piezoelectric effect as a device for sensing the oscillation of a resonating portion and inverting the oscillation to electric signals. However, such oscillation signal converting devices are not limited to those utilizing the piezoelectric effect, but may be constituted by those utilizing electromagnetic induction, change in electrostatic capacity, change in incident light, change in electric resistance, or pyroelectricity.

For example, those utilizing electromagnetic induction include those having a coil installed on the sensing plate, an electric circuit for detecting electric signals flowing in the coil, and a magnet (may be an electromagnet) for generating a magnetic field in the coil. In this case, when the coil oscillates together with the resonating portion, an electric current flows through the coil due to electromagnetic induction, and the electric current is detected by the electric circuit. Those utilizing change in electrostatic capacity include those having a pair of electrodes installed on the surface of the sensing plate, a dielectric sandwiched by these electrodes, and an electric circuit connected to these electrodes, and detecting the electrostatic capacity charged in this specific space with the electric circuit.

Those utilizing change in incident light include those having a device for illuminating the resonating portion such as a photodiode, and a device for measuring the quantity of light reflected by the resonating portion (light receiver). This light receiver may be a photo sensor. As the resonating portion oscillates, the quantity of light reflected by the resonating portion changes, and change in the quantity of the incident light is measured by the light receiver.

Those utilizing change in electric resistance are roughly divided into that using a conductor and that using a semiconductor. That using a conductor has a conductor provided on the surface of the resonating portion, and an electric circuit connected to the conductor. Since the conductor is distorted by oscillation when the conductor oscillates together with the resonating portion and its resistance changes, this change in resistance is detected by the electric circuit. That using a semiconductor uses a semiconductor in place of the conductor.

Those utilizing pyroelectricity include those comprising a pair of electrodes provided on the surface of the sensing plate, a pyroelectric member formed between these electrodes, an electronic circuit connected to the electrodes, and a heat source, and detecting pyroelectric current generated by oscillation with the electronic circuit.

These types of oscillation signal converters can be used in place of the piezoelectric elements described above, and in addition, different signal converters can be used for the excitation of the resonating portion and for receiving the oscillation from the resonating portion separately. For example, a piezoelectric converter can be used for exciting, and an electrostatic capacity-type converter for receiving. The arrangement of exciting and receiving devices can be selected suitably and conveniently depending on the number of sensing plates. For example, when only one sensing plate is used, they can be arranged on the surface of the sensing plate; when two sensing plates are used, they can be arranged on both surfaces of the two, or on each surface.

INDUSTRIAL APPLICABILITY

As described above, a mass sensor and a method for mass sensing of the present invention, exhibit excellent effects in that change in various extremely small masses occurring on a diaphragm, that is change in mass load on the diaphragm, can be sensed easily and accurately in a short time. Therefore, when a catching substance for catching various substances to be sensed is applied to the diaphragm, the mass sensor can be used as a gas sensor, taste sensor, odor sensor, immune sensor, or moisture meter, which can sense various chemical substances or microorganisms such as bacteria and viruses easily and quickly. When such a catching substance is not applied to the diaphragm, the mass sensor can be used as a film thickness meter, viscosity meter, vacuum meter, or thermometer. In addition, when the sensor is used as an immune sensor substituting the dyeing method, an odor sensor, or a taste sensor, the reliability of tests can be improved, because determination does not rely on human sense.

Also, since the mass sensor of the present invention is little affected by the temperature of the specimen or change in the properties of materials for the mass sensor itself due to the temperature of the specimen on sensing resonant frequencies, and can measure an extremely small quantity of a 0.1 nanogram order as the nature of its structure, it exhibits the effect for sensing an extremely small quantity of substance.

Furthermore, although the mass sensor of the present invention can be used for various applications as described above, since measurement is performed on the basis of fundamental measurement principle in which change in resonant frequencies of the resonating portion including the diaphragm subjected to mass load are measured, a plurality of resonating portions having different functions can be provided in a mass sensor easily. Therefore, since the use of a plurality of various discrete sensors is not required, the mass sensor of the present invention also excels in economic effects in the reduction of costs for incorporating the sensor in the measuring location, for facilities for handling or measuring such as measuring instruments, as well as the reduction of costs by the integration and the shared use of manufacturing equipments.

The invention claimed is:

1. A method for sensing a mass with a mass sensor comprising the steps of:
   providing a mass sensor comprising
      a sensor substrate having one of a depression and a through-hole formed therein,
      a diaphragm extending from a first side thereof to a second side thereof in a first direction and extending from a third side thereof to a fourth side thereof in a second direction that is perpendicular to said first direction,
      a first connection plate having a first side that is joined to said sensor substrate at a side surface of said depression or said through-hole and having a second side that is joined to said first side of said diapraphm,
      a second connection plate having a first side that is joined to said sensor substrate at an opposed side surface of said depression or said through-hole and having a second side that is joined to said second side of said diaphragm such that said diaphragm is sandwiched between said first and second connection plates along said first direction and such that said diaphragm and said connection plates span the distance between the sides of the depression or the through hole along the first direction,
      a plurality of sensing plates joined to another side of said depression or said through-hole and one of (a) a third side of a respective one of said connection plates and (b) the third side of the diaphragm such that said sensor plates extend along the second direction between the respective third sides of the connection plates or the third side of the diaphragm and the another side of the depression or through-hole, and
      at least one piezoelectric element disposed on a surface of at least one of said plurality sensing plates; and
   determining said mass by measuring a resonant frequency of said mass sensor using said piezoelectric element during one of:
      a swing oscillation of said diaphragm centered on an axis passing along said first direction, oscillation parallel to said second direction and also perpendicular to said first direction; and
      a rotating oscillation of said diaphragm with respect to a surface of said diaphragm.

* * * * *